United States Patent [19]
Roy et al.

[11] Patent Number: 5,972,707
[45] Date of Patent: Oct. 26, 1999

[54] GENE DELIVERY SYSTEM

[75] Inventors: Krishnendu Roy, Baltimore; Hai-Quan Mao, Towson; Vu L. Truong; Thomas August, both of Baltimore; Kam W. Leong, Ellicot City, all of Md.

[73] Assignee: The Johns Hopkins University, Baltimore, Md.

[21] Appl. No.: 08/890,599

[22] Filed: Jul. 9, 1997

Related U.S. Application Data

[63] Continuation-in-part of application No. 08/657,913, Jun. 7, 1996, said application No. 08/657,913, Jun. 7, 1996, and a continuation of application No. 08/265,966, Jun. 27, 1994, abandoned.
[60] Provisional application No. 60/021,408, Jul. 9, 1996.
[51] Int. Cl.$^6$ ................................................. C12N 15/00
[52] U.S. Cl. ...................... 435/455; 435/320.1; 435/440; 514/44
[58] Field of Search ........................... 514/44; 435/172.3, 435/455, 440, 320.1

[56] References Cited

U.S. PATENT DOCUMENTS

| | | | |
|---|---|---|---|
| 4,885,172 | 12/1989 | Bally et al. | 424/417 |
| 4,948,590 | 8/1990 | Hawrot et al. | 424/450 |
| 5,008,116 | 4/1991 | Cahn | 424/491 |
| 5,166,319 | 11/1992 | Wrasidlo | 530/391.1 |
| 5,216,130 | 6/1993 | Line et al. | 530/362 |
| 5,258,499 | 11/1993 | Konigsberg et al. | 530/351 |
| 5,279,833 | 1/1994 | Rose | 424/450 |
| 5,393,527 | 2/1995 | Malick et al. | 435/7.1 |
| 5,744,166 | 4/1998 | Illum | 424/501 |

FOREIGN PATENT DOCUMENTS

| | | |
|---|---|---|
| 9417786 | 8/1994 | WIPO . |
| 95/22963 | 8/1995 | WIPO . |
| 96/00295 | 1/1996 | WIPO . |
| 97/32572 | 9/1997 | WIPO . |

OTHER PUBLICATIONS

Orkin et al. Report and Recommendations of the Panel to Assess the NIH Investment in Research on Gene Therapy. Distributed by the National Institutes of Health, Bethesda, MD or www.nih.gov., Dec. 7, 1995.
Verma et al. Gene Therapy—Promises, Problems, and Prospects. Nature, vol. 389, pp. 239–242, Sep. 18, 1997.
Gao et al., J. Liposome Res., 3 (1), 1993, 17–30.
Verrijk et al., Cancer Chemo. Pharmacol., 29, 1991, 117–121.
Eldridge et al., Mol. Immunol., 28 (3), 1991, 287–294.
Miller et al., FASEB Journal, 9, 1995, 190–199.
Hodgson, exp. Opin., Ther. Pat., 5 (5), 1995, 459–468.
Davis et al., J. Contiolled Rel., 24, 1993, 157–163.
Cortesi et al., Int. J. Pharmaceut., 105, 1994, 181–186.
Culver et al., TIG, 10 (5), 1994 May, 174–178.
Marshall, Science, 269, 1995, 1050–1055.
Truong et al. Exp. Biology, 1993, Abstract No. 30838.
Leong et al., Exp. Biology, 1993, Abstract No. 30839.
Truong et al., Proc. Int. Symp. Control Rel. Biact. Mater., 20:474–475, 1993.
Derwent Publications ltd., London, GB; An 91–299437 P00205218 & JP 03 198 782 A. Aug. 29, 1991.
Roy, Krishnendu et al., "DNA–Chitosan Nangspheres: Transfection Efficiency and Cellular Uptake" Proc. Int. Symp. Controlled Release Bioact. Mater. (1997) 24th 673–674.
Mao, H.Q. et al., "DNA–chitosan nanospheres: derivatization and storage stability" Proc. Int. Symp. Controlled Release Bioact. Mater. (1997), 24th, 671–672.
Mao, H.Q. et al., "DNA–chitosan nanospheres for gene delivery" Proc. Int. Symp. Controlled Release Bioact. Mater. (1996), 23rd, 401–402.
Walsh, S.M. et al., "Combination of drug and gene delivery by gelatin nanospheres for the treatment of cystic fibrosis" Proc. Int. Symp. Controlled Release Bioact. Mater. 91997), 24th, 75–76.
Truong–Le, Vu L. Et al. "Delivery of DNA vaccine using gelatin–DNA nanospheres" Proc. Int. Symp. Control Release Bioact. Mater. 91997), 24th, 39–40.

*Primary Examiner*—Brian R. Stanton
*Assistant Examiner*—Deborah J. R. Clark
*Attorney, Agent, or Firm*—Banner & Witcoff, Ltd.

[57] ABSTRACT

A gene delivery system is made of enzymatically degradable polymeric cation and nucleic acid (DNA or RNA) nanospheres optionally with a linking moiety or a targeting ligand attached to the surface. The delivery system can be made by a simple method of coacervation. Targeting ligands can be attached to the nanosphere directly or via a linking moiety. The linkage design allows the attachment of any molecule onto the nanosphere surface including antibodies, cell adhesion molecules, hormones and other cell-specific ligands.

27 Claims, 22 Drawing Sheets

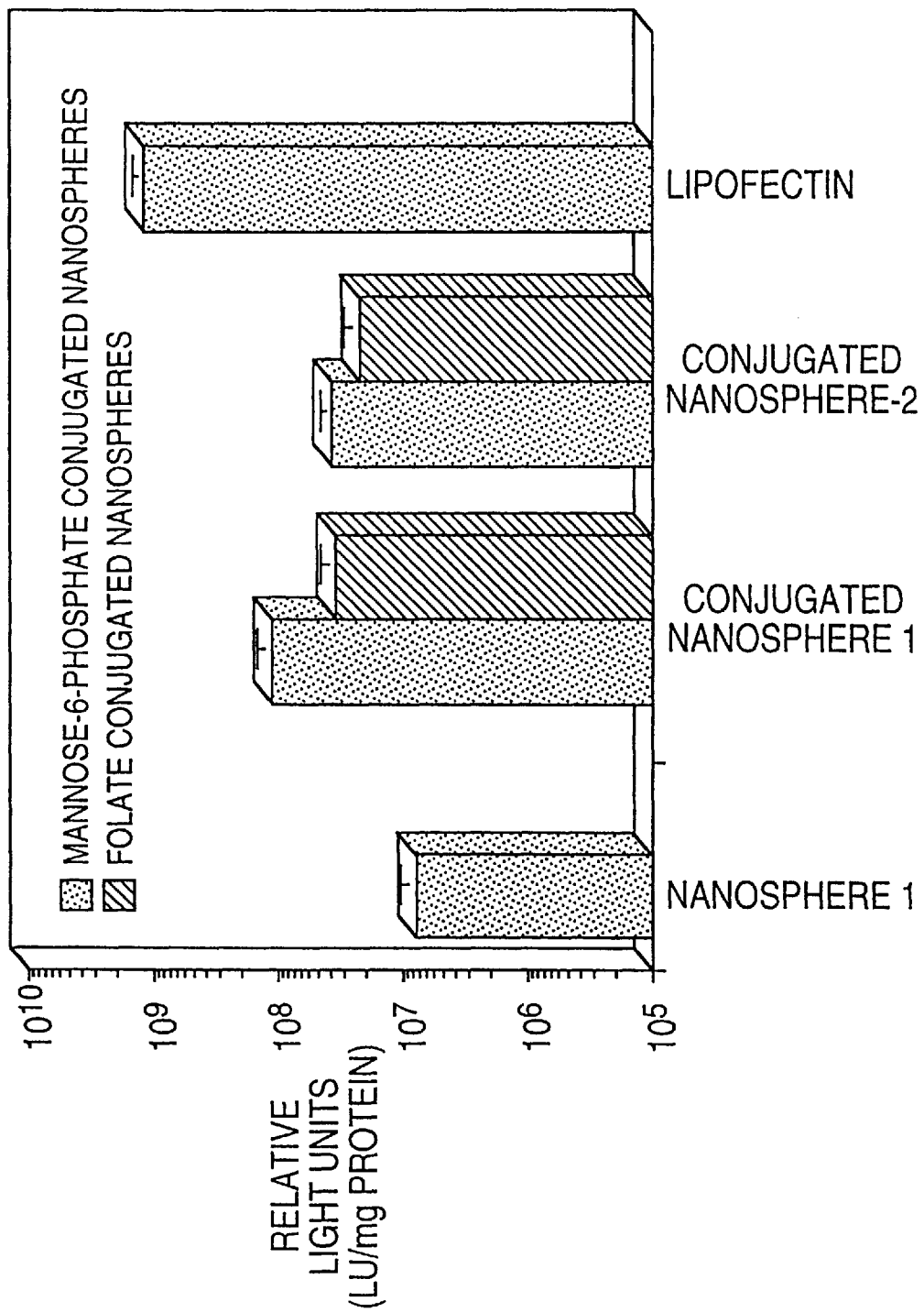

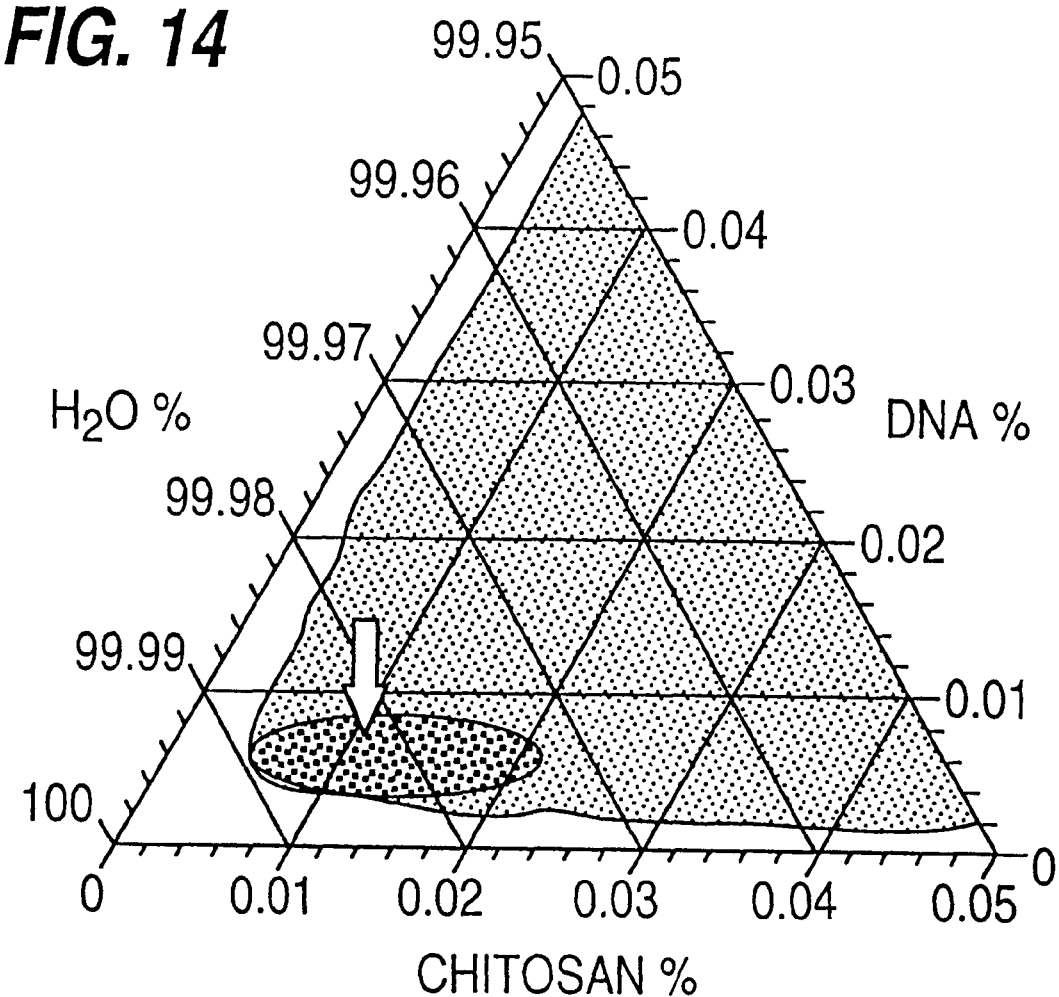

TEM: Scale Bar = 210 nm

SEM: Scale Bar = 356 nm

GENE DELIVERY SYSTEM

This application is a continuation-in part of Ser. No. 08/657,913 filed Jun. 7, 1996, and Ser. No. 60/021,408 filed Jul. 9, 1996, said Ser. No. 08/657,913, is a continuation of Ser. No. 08/265,966 filed Jun. 27, 1994 abandoned.

BACKGROUND OF THE INVENTION

A variety of techniques have been used to introduce foreign genes into cells. Physical methods include co-precipitation with calcium phosphate, electroporation, and particle bombardment. While these direct transfer techniques are adequate in vitro, they are impractical in vivo. Promising in vivo gene therapy relies on a carrier such as viral vectors or liposomes for delivery. There are still lingering safety concerns for viral vectors. Another limitation is the size of the DNA sequences, usually limited to 7–8 kb, that can be incorporated into the viral vector. Liposomes, on the other hand, have low loading level in general. In both cases, there is the issue of cell or tissue specificity for these gene delivery systems.

Controlled drug delivery has significantly improved the success of many drug therapies (Langer, R., 1990, New methods of drug delivery, *Science,* 249:1527–33; Poznansky, et al., 1984, Biological approaches to the controlled delivery of drugs: a critical review, *Pharmacol Rev.,* 36:277–336). A major goal of drug delivery is to localize the drug to the target site. These targeted delivery systems often take the form of injectables composed of liposomes (Gregoriadis, G., 1988, Liposomes as Drug Carriers, New York: Wiley; Litzinger, et al., 1992, Phosphatidylethanolamine liposomes: drug delivery, gene transfer and immunodiagnostic applications, *Biochimica et Biophysica Acta,* 1113:201–27) and microspheres made of proteins (Cummings, et al., 1991, Covalent coupling of doxorubicin in protein microspheres is a major determinant of tumor drug deposition, *Biochem. Pharm.,* 41:1849–54; Verrijik, et al., 1991, Polymer-coated albumin microspheres as carriers for intravascular tumor targeting of cisplatin, *Cancer Chemother. and Pharm.,* 29:117–21; Tabata, et al., 1988, Potentiation of antitumor activity of macrophages by recombinant interferon alpha A/D contained in gelatin microspheres, *Jpn. J. Cancer Res.,* 79:636–646), polysaccharides (Rongved, et al., 1991, Crossed-linked, degradable starch microspheres as carriers of paramagnetic resonance imaging: synthesis, degradation, and relaxation properties, *Carbohydrate Res.,* 145:83–92; Carter, et al., 1991, The combination of degradable starch microspheres and angiotensin II in the manipulation of drug delivery in an animal model of colorectal metastasis, *British J. Cancer,* 65:37–9), and synthetic polymers (Davis, et al., 1984, Microspheres and Drug Therapy, *Amsterdam;* Eldridge, et al., 1991, Biodegradable microspheres as a vaccine delivery system, *Molec. Immunology,* 28:287–94; Pappo, et al., 1991, Monoclonal antibody-directed targeting of fluorescent polystyrene microspheres to Peyer's patch M cells, *Immunology,* 73:277–80). Polymeric systems share some of the advantages of liposomal systems such as altered pharmacokinetics and biodistribution. While liposomes might have better prospects of biocompatibility and potential for fusion with cells, polymeric microspheres have more controllable release kinetics, better stability in storage, and higher drug-loading levels for some classes of compounds.

There is a need in the art for a DNA delivery system which can provide controlled release, is simple to make, is stable, is cost effective, has a high DNA loading level, and is relatively non-immunogenic.

SUMMARY OF THE INVENTION

It is an object of the invention to provide polymeric particles for delivery of DNA to cells.

It is an object of the invention to provide a method of making polymeric particles for delivery of DNA to cells.

It is another object of the invention to provide a method of delivering DNA to cells using polymeric particles.

These and other objects of the invention are provided by one or more of the embodiments described below. In one embodiment a nanosphere for gene delivery is provided. The nanosphere comprises a polymeric cation and DNA, and optionally a linking molecule or a targeting ligand is attached to the surface of said nanosphere.

In another embodiment of the invention a method of forming nanospheres for gene delivery is provided. The method comprises the steps of: forming nanospheres by coacervation of DNA and a polymeric cation; and optionally adhering a linking molecule or a targeting ligand to the surface of the nanospheres.

In yet another embodiment of the invention a method for introducing genes into cells is provided. The method comprises incubating cells to be transfected with solid nanospheres comprising a polymeric cation and DNA. Optionally a targeting ligand is attached to the nanosphere's surface. The targeting ligand binds to the surface of the cells to be transfected.

Thus the present invention provides the art with an attractive DNA delivery system which is simple to prepare, is cost effective, has controlled release ability, is storage stable, and is biocompatible.

BRIEF DESCRIPTION OF THE DRAWINGS

FIG. 3(A–B). Controlled release of intact LAMP-1 cDNA was demonstrated in vitro. The nanospheres were cross-linked with glutaraldehyde at various glutaraldehyde concentrations then degraded with trypsin.

FIG. 4. Fluorescent images of U937 cells transfected by controls and LAMP-1 cDNA-loaded nanospheres (at day 3 post-transfection).

FIG. 13. Transfection of HEK293 cells with mannose-6-phosphate or folate conjugated nanospheres. 8×cells were seeded into each well of a 12 well plate 24 hours before transfection. nanospheres containing 2 $\mu$g of DNA were incubated with the cells in each well for 4 hours. The cells were further incubated with fresh medium for 3 days, and luciferase expression levels were measured using a Promega luciferase assay system.

FIG. 14. Three-phase diagram for pRE-luciferase pcDNA-chitosan coacervation at 50 mM $Na_2SO_4$ and 55° C. The dark shaded area shows the concentration at which the nanosphere phase can be observed. Precipitation or aggregation occurs within the light area and there is no phase separation in the white area. The conditions used to prepare nanospheres are shown by the arrow. The final composition of the nanospheres are 34.65±0.95% by weight of plasmid DNA and 65.35±0.95% by weight of chitosan; their encapsulation efficiencies are 98±2.0% and 92.7±3.7%, respectively.

DETAILED DESCRIPTION OF THE PREFERRED EMBODIMENTS

Figure 1:
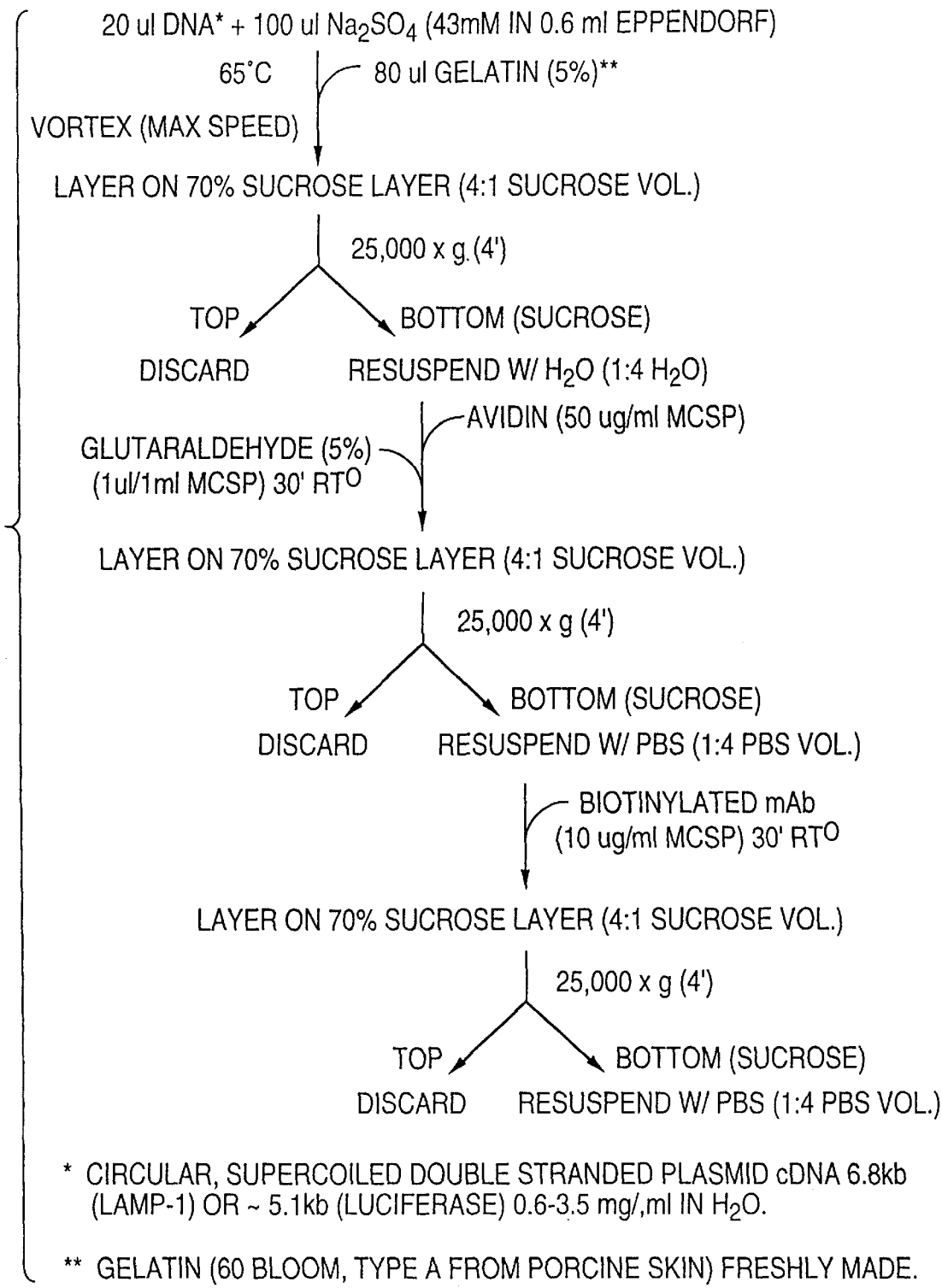
FIG. 1. Schematic diagram showing the synthesis of gelatin-DNA coacervates.

It is a discovery of the present invention that nucleic acid molecules of various chain lengths can complex with polymeric cations in aqueous conditions to form solid nanospheres ranging from submicron to microns in size. These nucleic acid-loaded nanospheres can efficiently transfect cells.

According to the present invention, a polymeric cation having a similar charge density to gelatin, is used to complex with nucleic acids to form nanospheres. Proteins such as tubulin, actin, cytochrome C, human serum albumin, and histones may be used as the polymeric cation. Polymeric amino acids, such as polyarginine and polylysine, may also be used, although natural proteins are preferred. Alternatively, carbohydrates such as chitosan, proteoglycan, methylcellulose, amylose, and starch can be used as the polymeric cation. Typically the polymeric cation has a molecular weight of between 5,000–1,000,000. Chitosan may be particularly useful as the polymeric cation of the present invention. Desirably sodium sulfate is used to induce the coacervation of polymeric cation and nucleic acids. Ethanol can also be used at a concentration of about 40 to 60% to induce coacervation.

Targeting ligands, if desired, can be directly bound to the surface of the nanosphere or can be indirectly attached using a "bridge" or "spacer". Because of the amino groups on some polysaccharides and on proteins (as provided by arginine and lysine groups of the proteins), the surface of the nanospheres can be easily derivatized for the direct coupling of targeting moieties. For example, carbodiimides can be used as a derivatizing agent. Alternatively, spacers (linking molecules and derivatizing moieties on targeting ligands) such as avidin-biotin can be used to indirectly couple targeting ligands to the nanospheres. Biotinylated antibodies and/or other biotinylated ligands can be coupled to the avidin-coated nanosphere surface efficiently because of the high affinity of biotin ($k_a \cong 10^{15}$ M$^{-1}$) for avidin (Hazuda, et al., 1990, Processing of precursor interleukin 1 beta and inflammatory disease, *J. Biol. Chem.*, 265:6318–22; Wilchek, et al., 1990, Introduction to avidin-biotin technology, *Methods In Enzymology*, 184:5–13). Orientation-selective attachment of IgGs can be achieved by biotinylating the antibody at the oligosaccharide groups found on the $F_C$ portion (O'Shannessy, et al., 1984, A novel procedure for labeling immunoglobulins by conjugation to oligosaccharides moieties, *Immunol. Lett.*, 8:273–277). This design helps to preserve the total number of available binding sites and renders the attached antibodies less immunogenic to $F_C$ receptor-bearing cells such as macrophages. Spacers other than avidin-biotin bridge can also be used, as are known in the art. For example, Staphylococcal protein A can be coated on the nanospheres for binding the $F_C$ portions of immunoglobulin molecules to the nanospheres.

Cross-linking can be used to stabilize nanospheres. This is particularly useful for protein-based nanospheres, such as those made of gelatin. The rate of nanosphere degradation and nucleic acid release can be designed a priori by varying the extent of cross-linking. Increased cross-linking yields increased stability of the nanosphere. The loading level of nucleic acid can be as high as 30% (w/w), with an encapsulation efficiency of >95%.

Cross-linking of linking molecules or targeting ligands to the nanosphere is used to promote the stability of the nanosphere as well as to covalently affix the linking molecule or targeting ligand to the nanosphere. The degree of cross-linking directly affects the rate of nucleic acids release from the microspheres. Cross-linking can be accomplished using glutaraldehyde, carbodiimides such as EDC (1-ethyl-3-(3-dimethylaminopropyl)-carbodiimide, DCC (N,N'-dicyclohexylcarbodiimide), carboxyls (peptide bond) linkage, bis (sulfosuccinimidyl) suberate, dimethylsuberimidate, etc.

Targeting ligands according to the present invention are any molecules which bind to specific types of cells in the body. These may be any type of molecule for which a cellular receptor exists. Preferably the cellular receptors are expressed on specific cell types only. Examples of targeting ligands which may be used are hormones, antibodies, cell-adhesion molecules, saccharides, drugs, and neurotransmitters.

The nanospheres of the present invention have good loading properties. Typically, following the method of the present invention, nanospheres having at least 5% (w/w) nucleic acids can be achieved. Preferably the loading is greater than 10 or 15% nucleic acids. Often nanospheres of greater than 20 or 30%, but less than 40 or 50% nucleic acids can be achieved. Typically loading efficiencies of nucleic acids into nanospheres of greater than 95% can be achieved.

The method of the present invention involves the coacervation of polymeric cations and nucleic acids. Because this process depends on the interaction of the positively charged polymeric cations and the negatively charged nucleic acids it can be considered as a complex coacervation process. However, sodium sulfate (or ethanol) induces the coacervation reaction by inducing a phase transition, and therefore it could also be considered as a simple coacervation reaction. Nucleic acids are present in the coacervation mixture at a concentration of between 1 ng/ml to 500 μg/ml. Desirably the nucleic acids are at least about 2–3 kb in length, and may range up to 10, 20, or 50 kb. Sodium sulfate is present at between 5 and 100 mM. Gelatin or other polymeric cation is present at between about 0.01 and 7%, preferably between 2 and 5% (w/v), in the coacervation mixture. Typically, about ten-fold higher amounts of amino acid-based polymers are required than carbohydrate based polymers. Thus gelatin is typically used at 1–5%, while chitosan is typically used at 0.01 to 0.05%. Using chitosan, suitable concentrations of nucleic acids are between 0.002% and 0.008%.

An attractive nanosphere delivery system requires a delicate balance among factors such as the simplicity of preparation, cost effectiveness, nucleic acids loading level, controlled release ability, storage stability, and immunogenicity of the components. The gene delivery system described here may offer advantages compared to other particulate delivery systems, including the liposomal system. The problems of instability, low loading level, and controlled release ability are better resolved with the polymeric nanosphere systems. Gelatin has received increasing biologic use ranging from surgical tissue adhesive (Weinschelbaum, et al., 1992, Surgical treatment of acute type A dissecting aneurysm with preservation of the native aortic valve and use of biologic glue. Follow-up to 6 years, *J. Thorac. Cardiovasc. Surg.*, 130:369–74) to quantitative immunohistochemical assays (Izumi, et al., 1990, Novel gelatin particle agglutination test for serodiagnosis of leprosy in the field, *J. Clinical Microbiol.*, 28:525–9) and as drug delivery vehicle (Tabata, et al., 1991, Effects of recombinant alpha-interferon-gelatin conjugate on in vivo murine tumor cell growth, *Cancer Res.*, 51:5532–8), due to its biocompatibility and enzymatic degradability in vivo. Compared to other synthetic polymeric systems, such as the extensively studied polylactic/polyglycolic copolymers, the mild conditions of nanosphere formulation are appealing. Unlike the solvent evaporation and hot-melt techniques used to formulate synthetic polymeric nanospheres, complex coacervation requires neither contact with organic solvents nor heat. It is also particularly suitable for encapsulating bio-macromolecules such as nucleic acids not only through passive solvent capturing but also by direct charge-charge interactions.

Unlike viral vectors, which cannot deliver genes larger than 10 kb, the nanosphere delivery system of the present invention does not have such size limitations. Nucleic acid molecules of greater than about 2 kb can be used, and nucleic acid molecules even from 10 to 50 kb may be used.

In general, the range of possible targets is dependent on the route of injection, e.g., intravenous or intraarterial, subcutaneous, intra-peritoneal, intrathecal, etc. For systemic injections, the specificity of this delivery system is affected by the accessibility of the target to blood borne nanospheres, which in turn, is affected by the size range of the particles. Size of the particles is affected by temperature, component concentration, and pH in the coacervation mixture. The particles can also be size-fractionated, e.g., by sucrose gradient ultracentrifugation. Particles with size less than 150 nanometers can access the interstitial space by traversing through the fenestrations that line most blood vessels walls. Under such circumstances, the range of cells that can be targeted is extensive. An abbreviated list of cells that can be targeted includes the parenchymal cells of the liver sinusoids, the fibroblasts of the connective tissues, the cells in the Islets of Langerhans in the pancreas, the cardiac myocytes, the Chief and parietal cells of the intestine, osteocytes and chondrocytes in the bone, keratinocytes, nerve cells of the peripheral nervous system, epithelial cells of the kidney and lung, Sertoli cells of the testis, etc. The targets for particles with sizes greater than 0.2 microns will be confined largely to the vascular compartment. Here, the targetable cell types include erythrocytes, leukocytes (i.e. monocytes, macrophages, B and T lymphocytes, neutrophils, natural killer cells, progenitor cells, mast cells, eosinophils), platelets, and endothelial cells.

For subcutaneous injections, the targetable cells include all cells that resides in the connective tissue (e.g., fibroblasts, mast cells, etc.), Langerhans cells, keratinocytes, and muscle cells. For intrathecal injections, the targetable cells include neurons, glial cells, astrocytes, and blood-brain barrier endothelial cells. For intraperitoneal injection, the targetable cells include the macrophages and neutrophils.

Carbohydrate-based nanospheres such as those made using chitosan offer many advantages. Cross-linking is not required. In addition, a targeting ligand is not required, although it can be used. Although applicants do not wish to be bound by any particular theory, it is postulated that cells have a receptor to which chitosan binds. The concentration of DNA required in the coacervation mix using chitosan is about half of that required using gelatin. In addition, the concentration of chitosan required is about one tenth that required for making gelatin nanospheres. Chitosan based nanospheres can be freeze dried and are storage stable.

Because chitosan-based nanospheres need not be cross-linked or reacted with targeting ligands, they can be readily used after formation without the need for extensive post-synthesis purifications. Elimination of this post-synthesis processing permits the direct use of freshly made coacervates to transfect cells. An additional contrast between chitosan- and gelatin-based nanospheres is the effect of chloroquine on transfection efficiencies. In the gelatin system, chloroquine improves the transfection efficiency. However, in the chitosan system, chloroquine does not improve the transfection efficiency. The size of the nanospheres is believed to be critical for efficient cellular delivery. Typically the nanospheres are less than 4, 3, 2, or even 1 μm. Most preferably the solid particles are between 200 and 300 nm.

EXAMPLES

Example 1

Matrix Materials: Gelatin (60 bloom, type A from porcine skin), chondroitin 4-sulfate, glutaraldehyde (25%, grade 1), 1-ethyl-3-(3-dimethylaminopropyl)carbodiimide hydrochloride (EDC hydrochloride), and ultra-pure sucrose were purchased from Sigma Chemical Co. (St. Louis, Mo.). Biotin LC hydrazide, and NeutrAvidin, and Coomassie protein assay reagents were from Pierce (Rockford, Ill.). Centricon microconcentrators were from Amicon (Beverly, Mass.).

Monoclonal antibodies: mAb PLM-2, a BALB/c mouse anti-porcine LFA-1 (IgG$_{1k}$) which also cross reacts with murine LFA-1, was isolated and purified as previously described (Hildreth, et al., 1989, Monoclonal antibodies against porcine LFA-1: species cross-reactivity and functional effects of b-subunit-specic antibodies, *Molec. Immunol*, 26:883–895). IB-4B, a rat anti-mouse LAMP-1 ascite fluid and a mouse anti-Luman CD44 mAb were isolated as previously described (de Wet, et al., 1987, Firefly luciferase gene: structure and expression in mammalian cells, *Mol. & Cell. Biol.*, 7:725–37). CHA is a IgG$_1$ that does not recognize any known in vivo mouse epitopes (Hybritech Inc., San Diego, Calif.). Affinity-purified FITC and Texas Red-labeled polyclonal anti-rat IgGs were obtained from Sigma.

Genes: Two genes were used to demonstrate the feasibility of this delivery system. The LAMP-a cDNA is a 6.4 kb circular supercoiled plasmid cDNA with a mouse LAMP-1 gene (2.4 kb) inserted into an Invitrogen plasmid cDNA with a CMV promoter (Guaarnieri, et al., 1993, *J. Biol. Chem.*, 268:1941). Detection of LAMP-1 expression was done by staining cells with anti-LAMP-1 mAb and with secondary anti-IgG mAb conjugated with Texas Red. The gene coding for luciferase enzyme is widely used in cell biology for the study of gene expression because of the high sensitivity of the assay, its simplicity, and low cost. In addition, the enzyme is a good reporter of gene expression because it is a cytosolic protein that does not require post-translational processing for enzymatic activity (de Wet, et al., 1987, Firefly luciferase gene: structure and expression in mammalian cells, *Mol. & Cell. Biol.*, 7:725–37; Wood, et al., 1989, Introduction to beetle luciferases and their applications, *J. of Biolumin. & Chemilum.*, 4:289–301). The presence of luciferase can be readily detected by an enzymatic reaction that involve the oxidation of beetle luciferin with concomitant production of a photon (in the form of chemiluminescence.) The assay was carried out using an assay kit purchased from Promega Corp. (Macison, Wis.).

Synthesis of microspheres: A detailed schematic diagram for the synthesis of the gelatin-DNA coacervates is shown in FIG. 1. All concentrations described are final concentrations in the reaction mixture set at 67° C. unless otherwise stated. Gelatin/plasmid DNA nanospheres coated with avidin were synthesized by first preparing a 3.5 mg/ml solution of plasmid DNA encoding a lysosomal associated membrane protein-1 (LAMP-1) (6.7 Kb, circular supercoiled) in 42 mM sodium sulfate (Na$_2$SO$_4$). Coacervation was initiated by the addition of gelatin (5%) to the DNA/Na$_2$SO$_4$ solution at equal volume while vortexing at high speed for 1 minute. Coencapsulation of drugs and other agents can be achieved by adding directly to the DNA/Na$_2$SO$_4$ solution before initiating coacervation with gelatin. Avidin (5 mg/ml) was added to the microsphere suspension at a final concentration of 75 ug avidin/ml microsphere solution. The microspheres mixture was layered onto a layer of 70% sucrose (w/v) and centrifuged at 6,000×g for 4 minutes (Brinkman Instruments Inc., Westbury, N.Y., model L8-75). Microsphere fractions recovered from the sucrose layer was diluted 5-fold with water then cross-linked with glutaraldehyde (12.5 mM final concentration) for 10 minutes at room temperature. Unreacted glutaraldehyde was quenched by adding ethanolamine (1 M) for 10 minutes. The microspheres were dialyzed by sucrose centrifugation as described above.

Attachment of biotinylated mAbs to avidin-coated microspheres: 30 ug of antibodies (biotinylated according to established procedures (O'Shannessy, et al., 1984, A novel procedure for labeling immunoglobulins by conjugation to oligosaccharides moieties, *Immunol. Lett.*, 8:273–277)) was added to 1 ml of avidin-coated microspheres suspension (11 mg/ml) for 1 hour with gentle agitation. Unbound mAb was removed from microspheres by dialysis.

Figure 2:
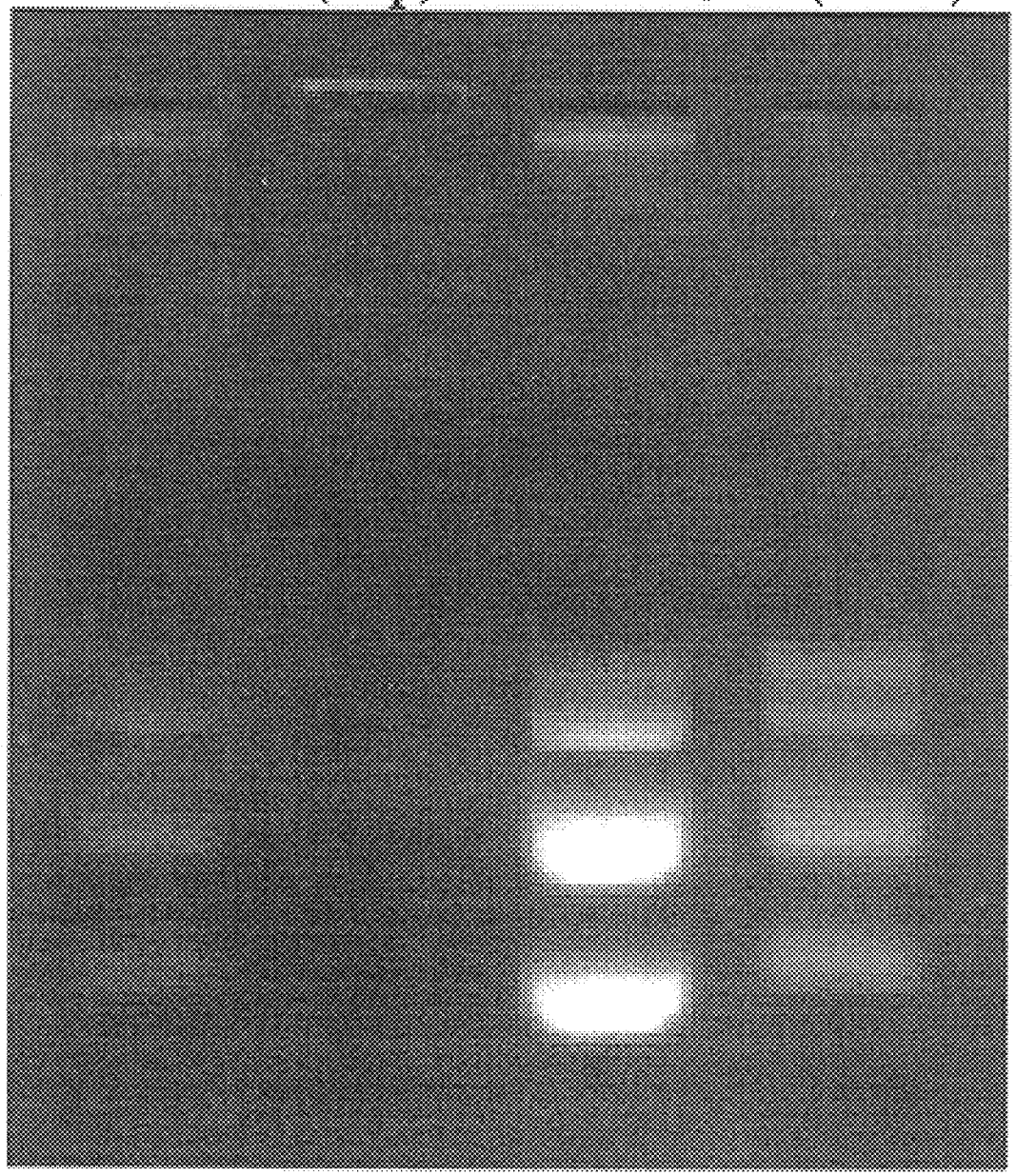
FIG. 2. Gel electrophoresis of cDNA before and after encapsulation. (std=standard; Sup=supernatant, Pellet= nanospheres pelleted by centrifugation).
Figure 3A:
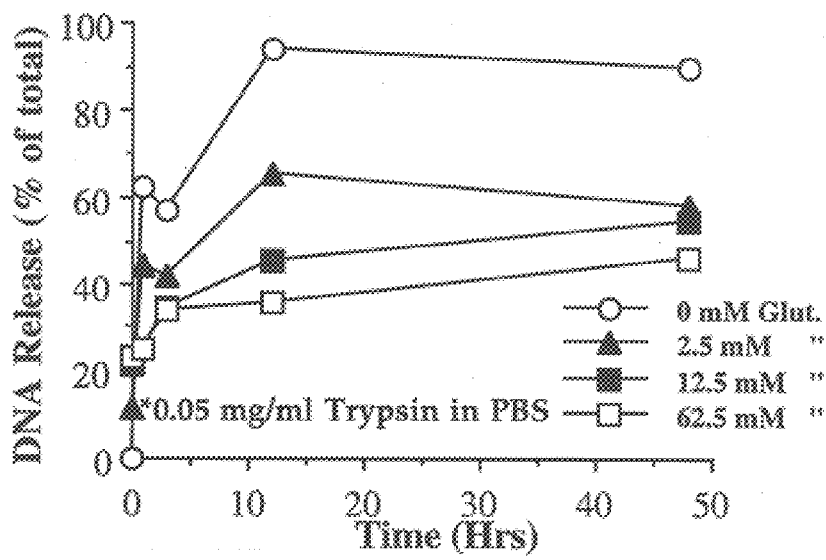
FIG. 3A shows the time course of DNA release at various glutaraldehyde-cross-linking levels.
Figure 3B:
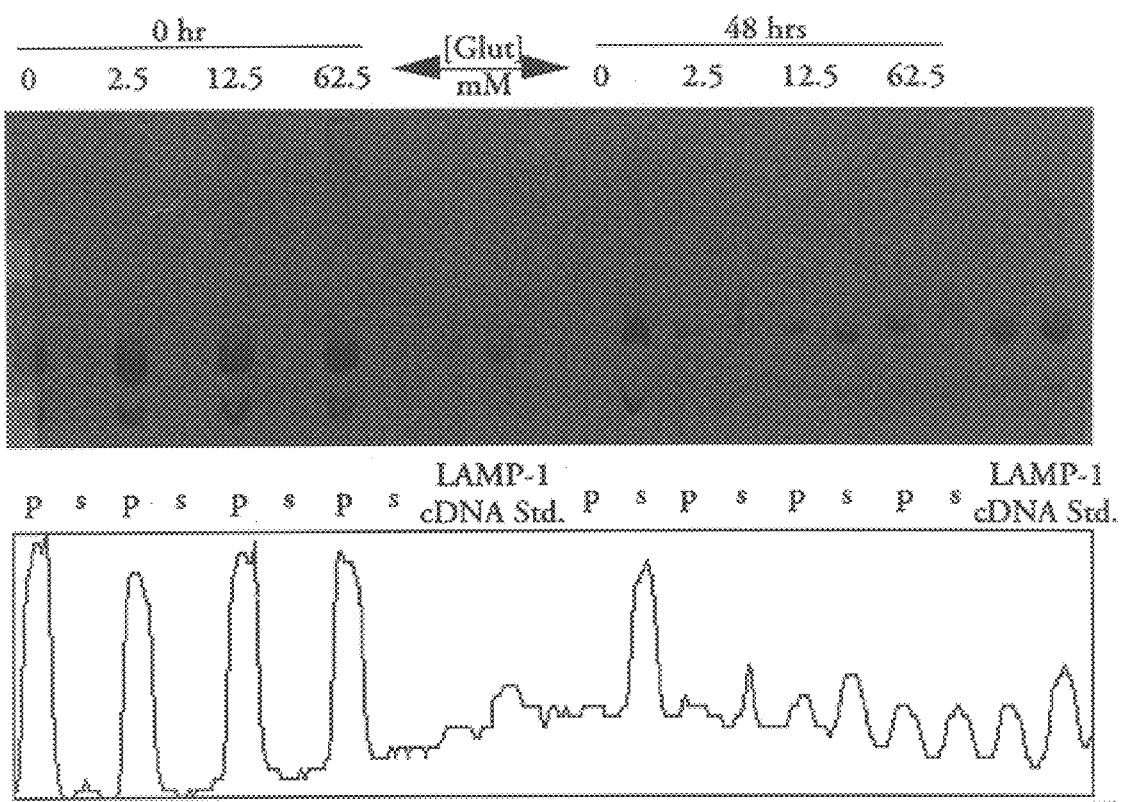
FIG. 3B shows (on gels and densitometer tracing) the DNA which was released from the nanospheres at various times and at various levels of glutaraldehyde-cross-linking.

Characterization of microsphere and binding performance: DNA loaded microspheres exhibited polymorphic colloid shape with a polydispersed particle size of less than 3 microns as determined by light microscopy. Purified microspheres were stable for at least one month without appreciable degradation. The loading level for LAMP-1 plasmid DNA was 20% (w/w). The encapsulation efficiency was typically>95%. The mobility of the free LAMP-1 DNA and the released DNA (from the microsphere) in 1% agarose gel electrophoresis were identical (FIG. 2), suggesting that the encapsulated DNA was released in its original form. Release rate of the cDNA from the microspheres was dependent on the cross-linking density and on the enzyme level (FIG. 4). Sustained release of up to weeks can be readily obtained.

Figures 4A, 4B, 4C, 4D:
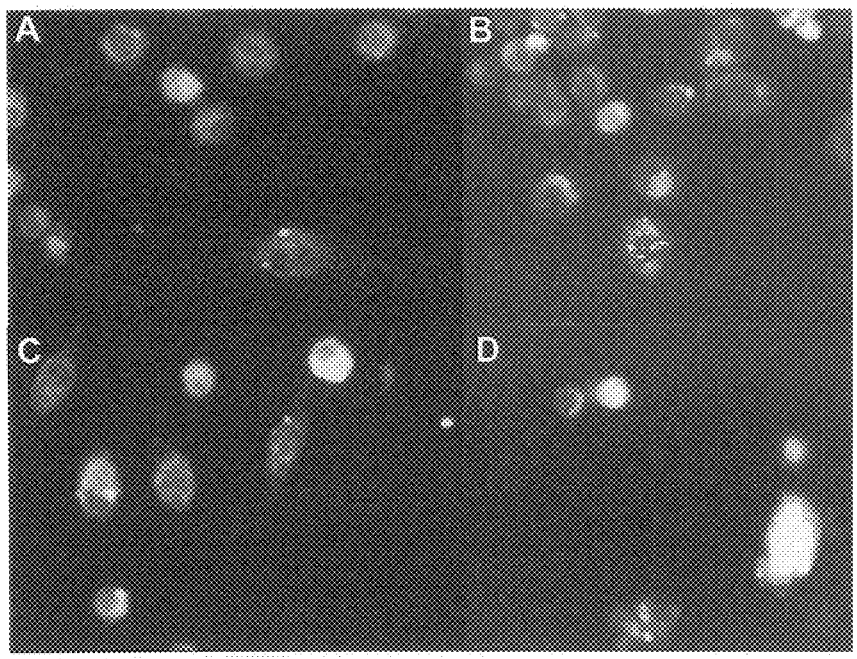
FIG. 4A: anti-DC44 nanospheres without cDNA.
FIG. 4B: calcium phosphate transfection.
FIG. 4C: LAMP-1 nanospheres without antibody.
FIG. 4D: LAMP-1 nanospheres coated with anti-CD44 mAB. LAMP-1 expression is manifested as granules (in lysosomes) in the cells.

We tested the ability of the LAMP-1 DNA loaded microspheres to bind and subsequently transfect a human histiocytic lymphoma cell line (U937) in tissue culture. When coated with either anti-LEA or anti-CD44 monoclonal antibody (both protein targets were expressed in high amount of U937 cell surface), expression LAMP-1 protein was detected by day 3 (FIG. 4A, fluorescent granules) when stained with antibodies recognizing LAMP-1. The staining pattern of U937 cells incubated with LAMP-1 microspheres was identical to the calcium phosphate method of transfection (FIG. 4B). Microspheres that were either coated with avidin or non-specific CHA mAb showed no granular staining patterns, and were identical to untreated cells (FIG. 4C).

Figure 5:
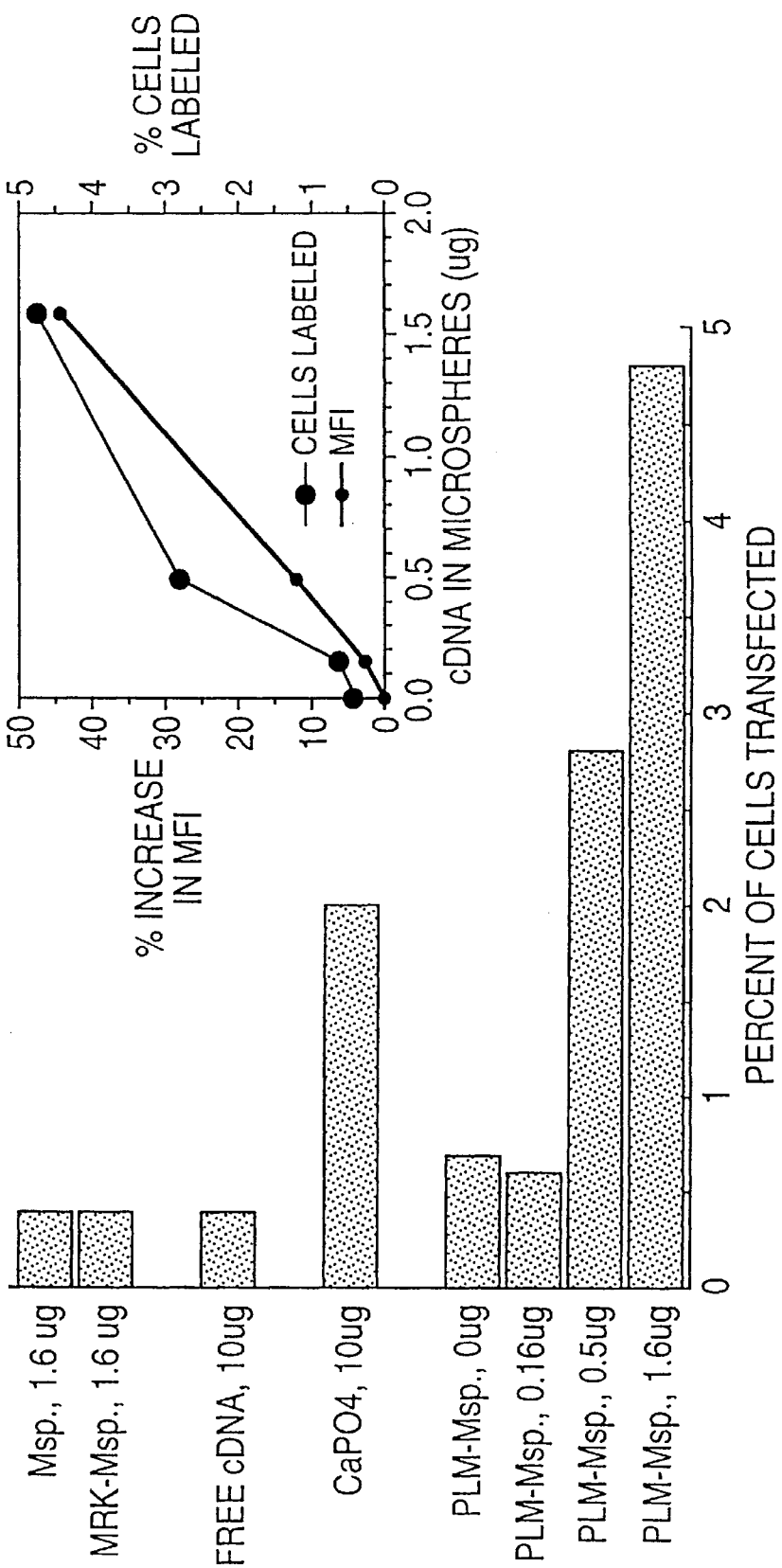
FIG. 5. Flow cytometric analysis of the transfection efficiency of U937 cells by antilymphocyte function associated antigen-1 coated nanospheres and controls. The actual mean fluorescence intensity (MFI) is shown in the insert. Msp=microspheres, MRK=a mismatched anti-P-glycoprotein antibody, PLM=anti-LFA antibody FIG. 6. Temporal expression of LAMP-1 in 293s cells transfected by anti-CD44 coated nanospheres.
Figure 6:
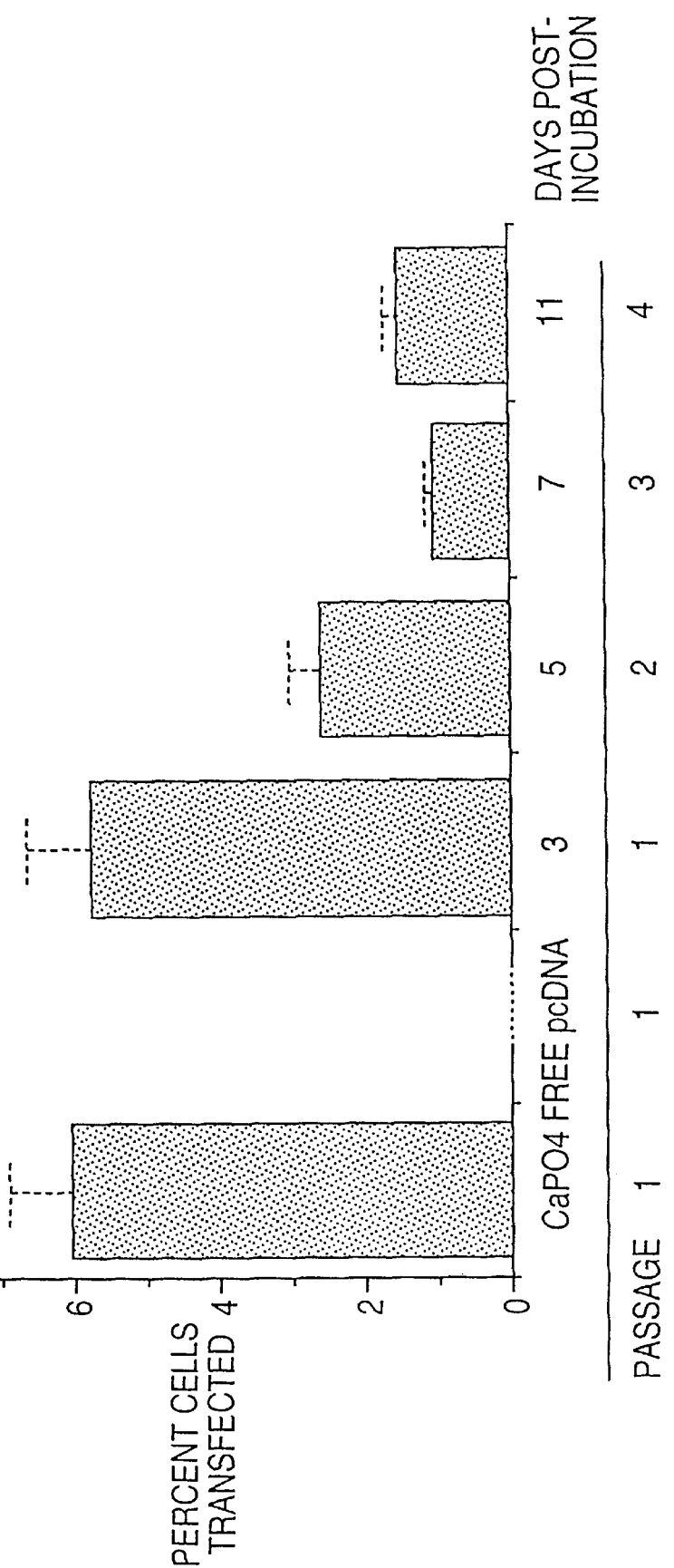

Using flow cytometry, we showed that the expression of LAMP-1 was detected in up to 5% of U937 cells in culture (FIG. 5). None of the controls—blank microspheres, microspheres with cDNA but no antibodies, microspheres with cDNA and coated with a mismatched anti-P-glycoprotein antibody (MRK-Msp.), and free cDNA at a concentration six time higher than entrapped in the microspheres—showed any evidence of transfection. The efficiency of transfection appears to be dose-responsive. In general, the transfection efficiency of this particular gene and cell type is comparable between the proposed microspheric delivery system (1–10%) and the calcium phosphate precipitation method (2–15%). FIG. 6 demonstrates the concept in a different cell type using a different monoclonal antibody. Again, free cDNA could not transfect the cells. Eventually the LAMP-1 expression disappeared after several passages. Positive results were also obtained for the luciferase reporter gene system. Transfection was clearly detected by measurement of luciferase enzymatic activity, in 293s cells incubated with luciferase gene-loaded microspheres.

Example 2

Figure 7:
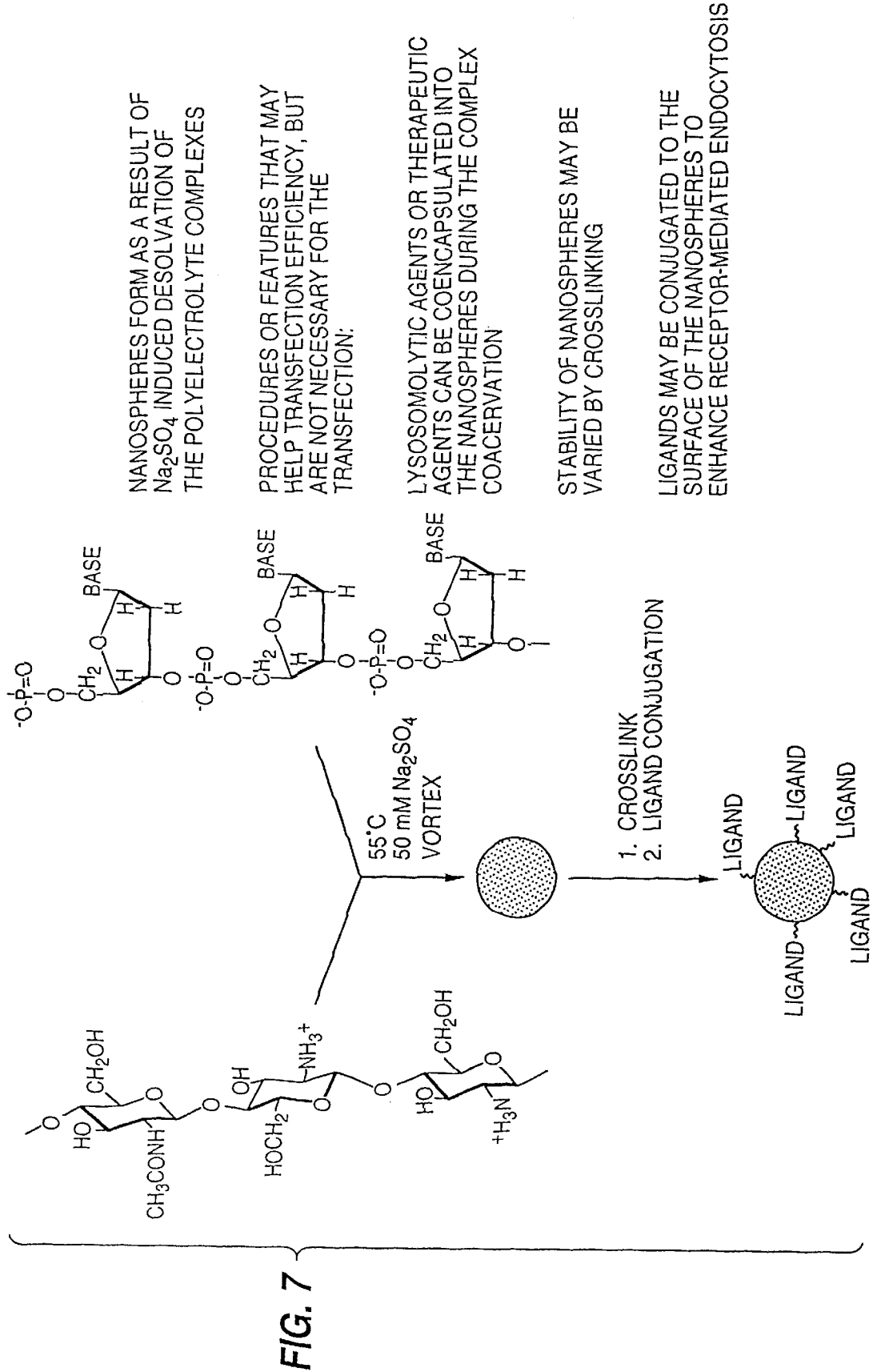
FIG. 7. Preparation of DNA-chitosan nanospheres by complex coacervation. Nanospheres form as a result of $Na_2SO_4$ induced desolvation of the polyelectrolyte complexes. Procedures or features that may help transfection efficiency, but are not necessary for transfection include: the coencapsulation of lysosomolytic agents or therapeutic agents into the nanospheres during the complex coacervation; varying the cross-linking to affect the stability of nanospheres; conjugation of ligands to the surface of the nanospheres to enhance receptor-mediated endocytosis.
Figure 8:
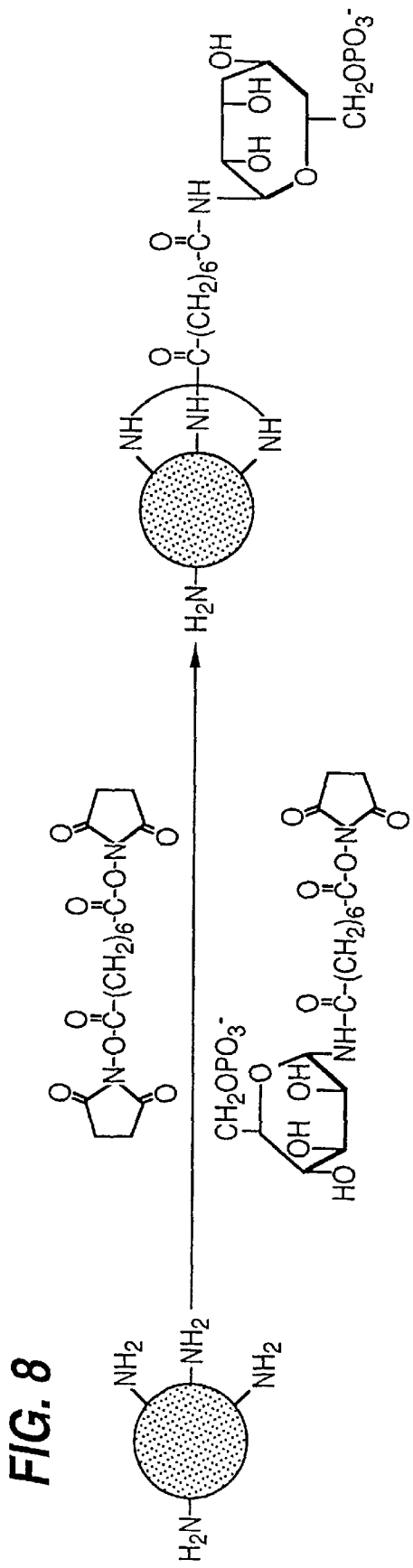
FIG. 8. The chemistry of coupling of mannose-6-phosphate to the surface of a DNA-nanosphere using carbodiimides.
Figure 9:
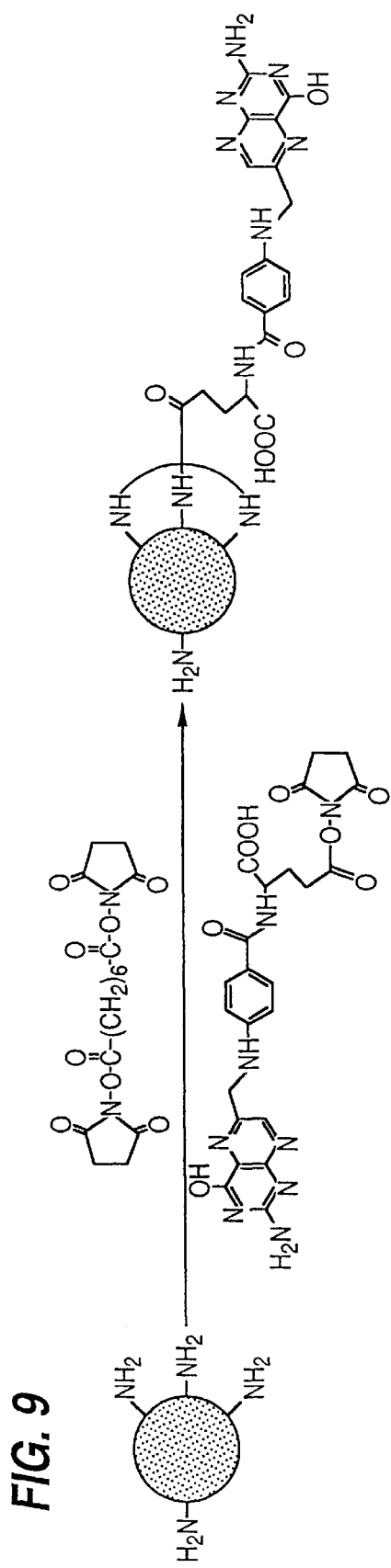
FIG. 9. The chemistry of coupling of folate to the surface of a DNA-nanosphere using carbodiimides.
Figure 10:
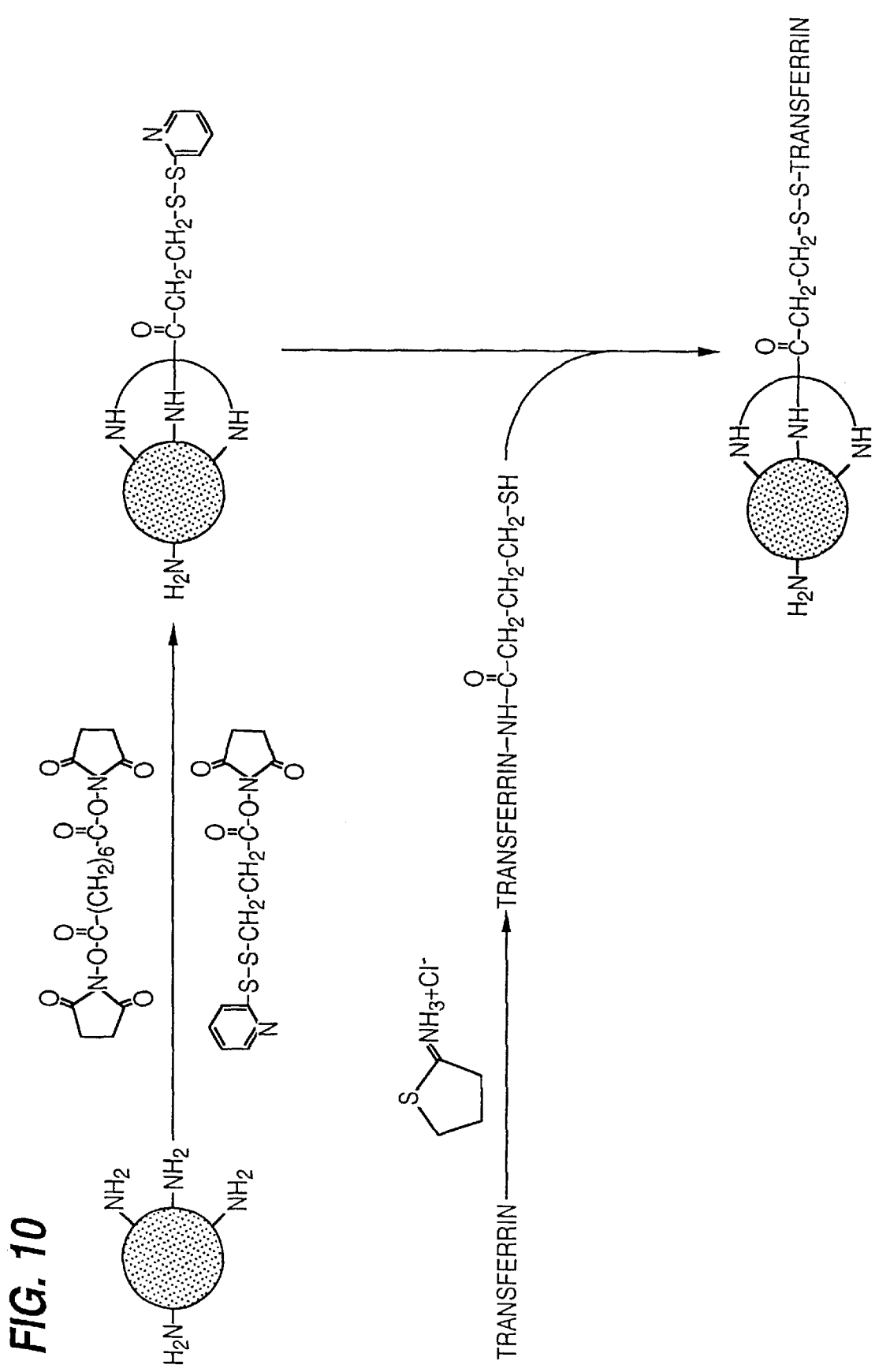
FIG. 10. The chemistry of coupling of transferrin to the surface of a DNA-nanosphere using carbodiimides.
Figure 11:
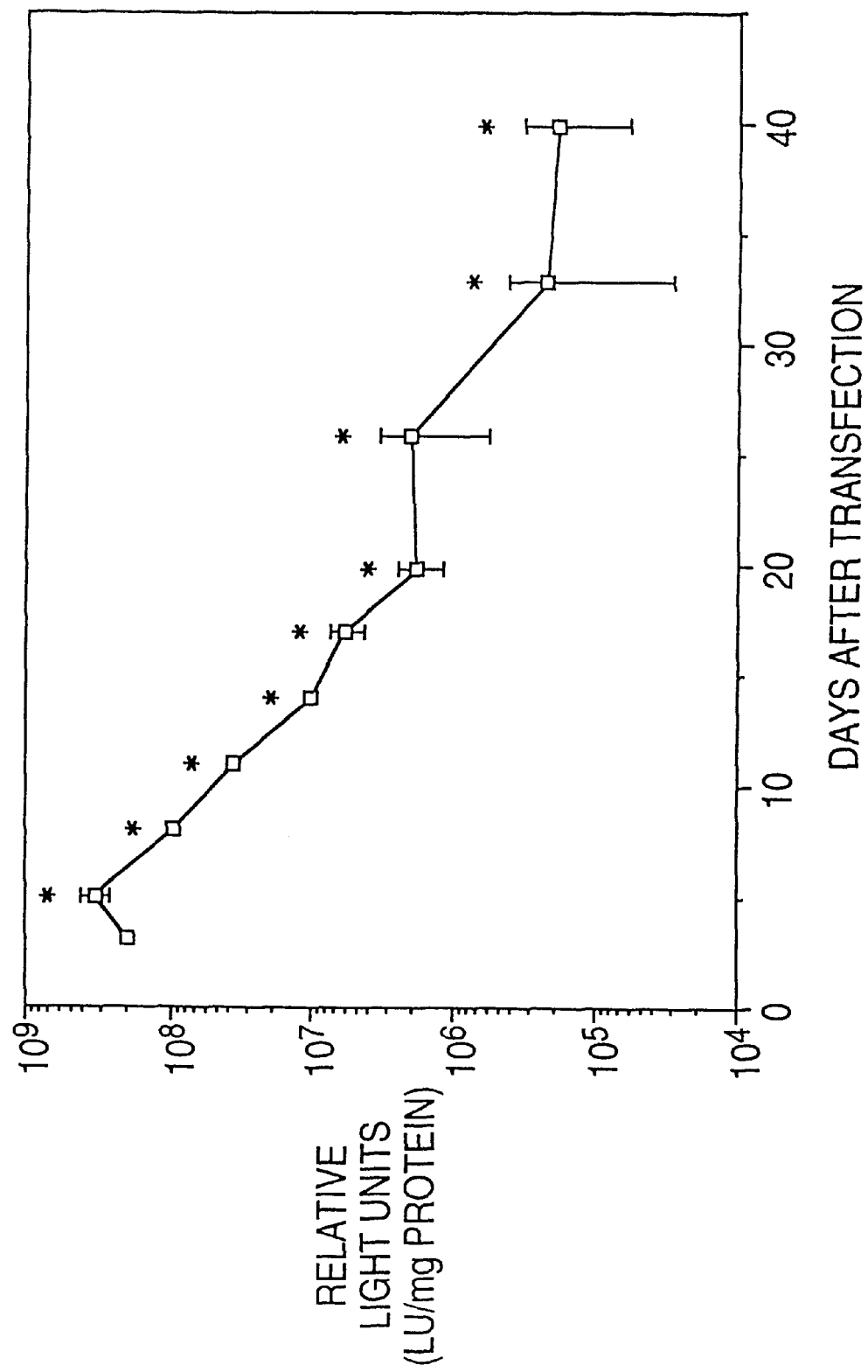
FIG. 11. The persistence of luciferase expression in HEK293 cells after transfection with DNA-chitosan nanospheres is demonstrated. $8 \times 10^4$ HEK293 cells were seeded into each well plate 24 hours before transfection, nanospheres containing 1 $\mu$g of DNA were incubated with the cells in each well for 4 hours. The cells were further incubated with fresh medium. After 5 days, the cells were passaged at 1:5 dilution every 3–7 days (indicated by an asterisk in the figure). Luciferase activities were measured at different time points.
Figure 12:
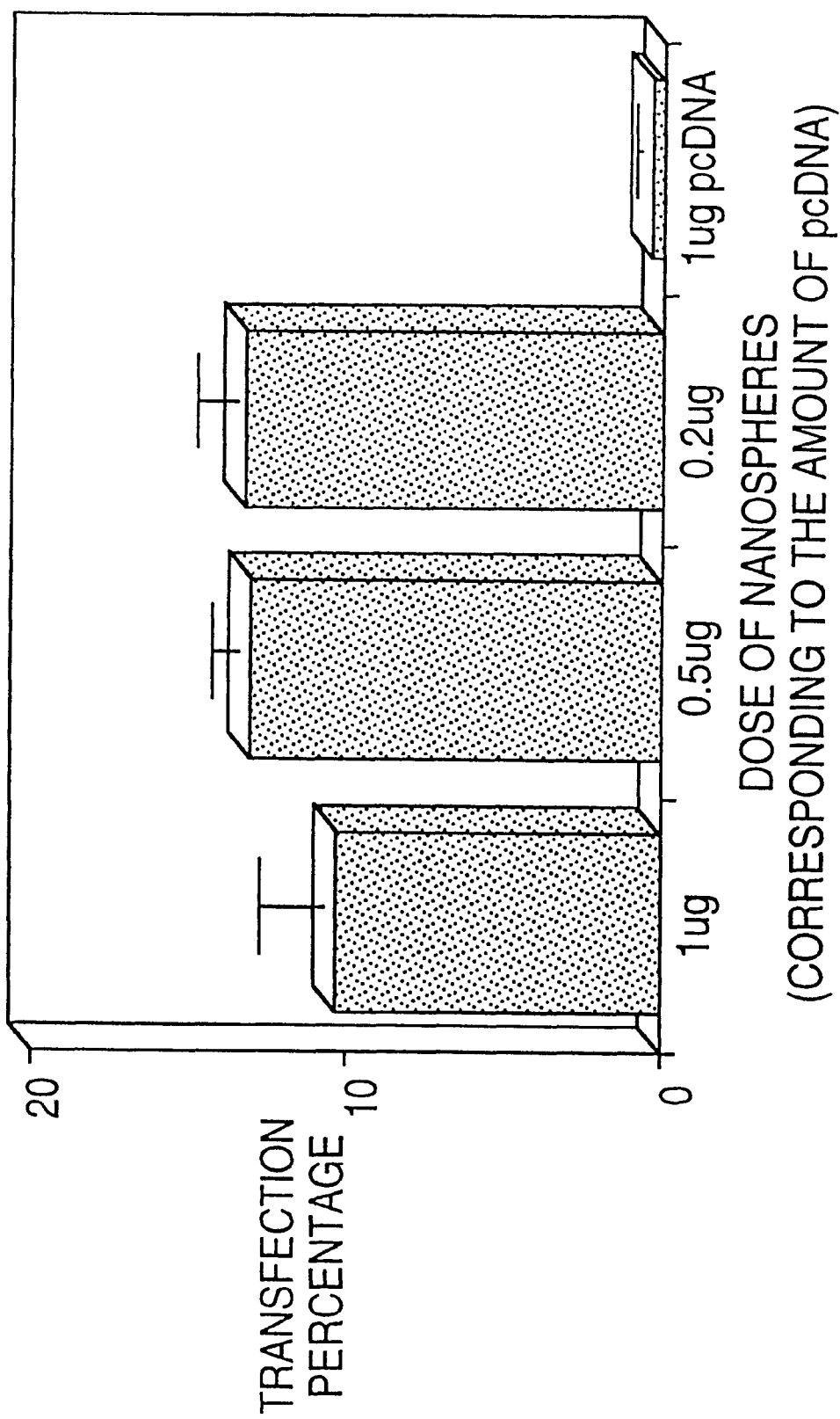
FIG. 12. Expression of green fluorescence protein in HEK293 cells after transfection with chitosan nanospheres containing pDI-neoGFP plasmid $8 \times 10^4$ HEK293 cells were seeded into each well of 12 well plate 24 hours before transfection, nanospheres containing 1 mg of DNA were incubated with the cells in each well for 4 hours. The cells were further incubated with fresh medium for 3 days, trypsinized and analyzed on a FACScan analyzer. The percentage of positive cells (transfection percentage) versus the amount of nanospheres is shown.

The general concept of synthesizing the DNA nanospheres is shown in FIG. 7.

DNA-gelatin nanospheres were synthesized by vortexing 100 ml of a solution containing gelatin (5% w/v in distilled water) and 4 mM chloroquine with 100 ml of a solution containing 0.2 mg/ml plasmid DNA and 4.3 mM sodium sulfate ($Na_2SO_4$) at 55° C. for one minute. Nanospheres without chloroquine were synthesized similarly except with a higher $Na_2SO_4$ concentration (45 mM). The unreacted components were removed by centrifuging the mixture in a 100 ml sucrose layer (55% w/w) at 40,000×g for 7 minutes. The sucrose fraction containing the nanospheres was diluted with water to 200 ml, then crosslinked and conjugated with transferrin by adding the nanosphere and transferrin solution (20 mg) to 22 ml of a 0.2 M MES buffer solution, pH 4.5, containing 0.1 mg/ml of (1-ethyl-[3-diethylaminopropyl]-carbodiimide hydrochloride) (EDC). The reaction was carried out in room temperature for 30 minutes, then quenched by addition of glycine reaching a 0.2 M final concentration. Crosslinking was also achieved by reaction with various concentrations of glutaraldehyde for 10 min. DNA-chitosan nanospheres were prepared similarly with the exception that the chitosan solution diluted to 0.02% (w/v, pH5.5 in 5 mM NaAc-HOAc).

Example 3

Figure 15A:
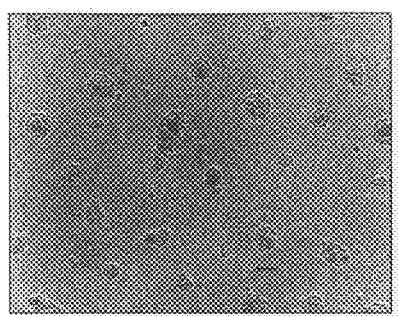
FIG. 15(A–C). Size distribution of chitosan-based nanospheres is shown as determined by Dynamic Light Scattering and Photon Correlation Spectroscopy. The size of the nanospheres clustered tightly between 200 and 300 nm.
Figure 15B:
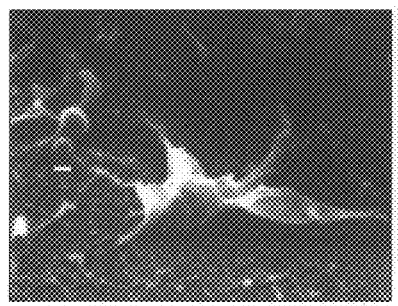
Figure 15C:
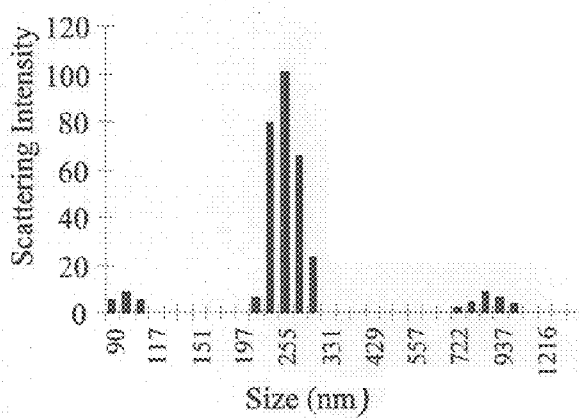

The general concept of synthesizing DNA nanospheres is shown in FIG. 7. Microparticular coacervates of chitosan or gelatin-DNA complexes formed as a result of $Na_2SO_4$-induced desolvation of the local water environment of the polyelectrolytes. Synthesis of the nanospheres was optimized with respect to salt concentration, pH, temperature, and reactant concentrations, as shown in the three-phase diagram of FIG. 14. At 55° C., pH 5.5, and a sodium sulfate concentration of 50 mM, phase separation of particulate chitosan-DNA complexes occurred at the concentration range of 0.005 to 0.02% (w/v) for chitosan, and 0.004 to 0.008% for the DNA. As shown by TEM and SEM in FIG. 15, nanospheres in the range of 200–320 nm were formed.

Figure 16:
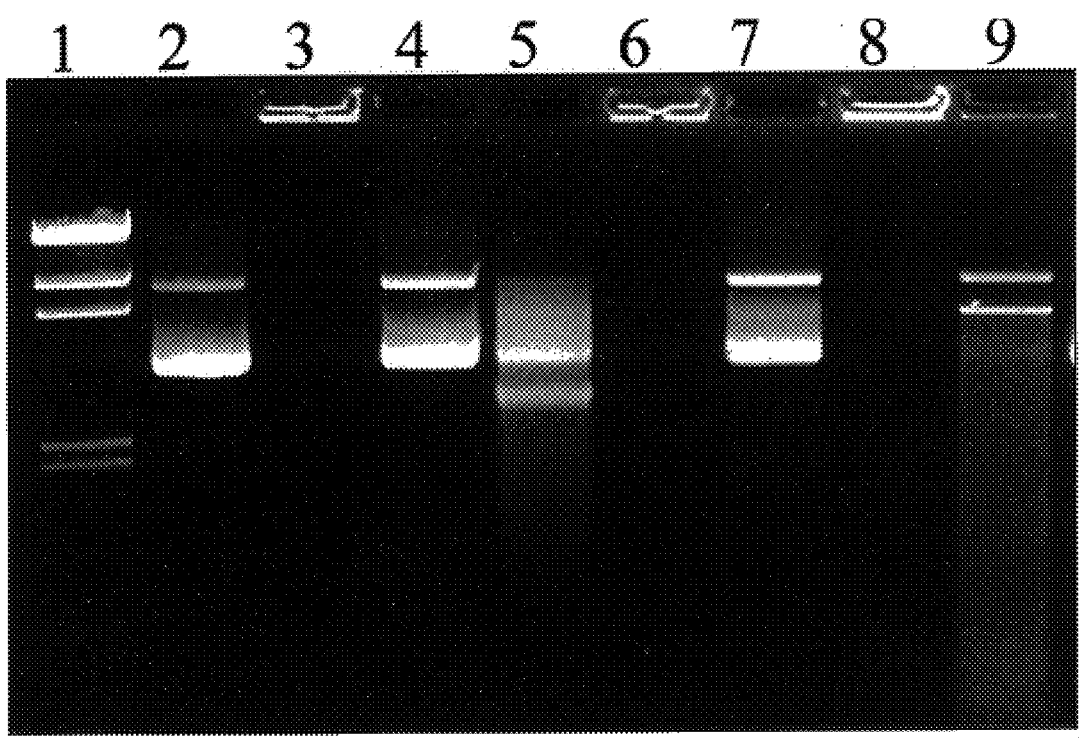
FIG. 16. Nanosphere formulation protects plasmid DNA from DNase I digestion. Naked DNA and nanospheres were both incubated with different concentrations of DNaseI for 15 min. At 37° C. The reaction was stopped with iodoacetic acid, a DNase I inhibitor. The nanospheres were then digested with chitosanase and lysozyme for 2 hours. All samples were run on an 0.08% polyacrylamide gel and stained with ethidium bromide. Lane 1: molecular weight markers; lane 2: plasmid; lane 3: nanospheres; lane 4: digested nanospheres; lane 5: plasmid+DNAse (0.1 $\mu$g); lane 6: nanospheres+DNAse (0.1 $\mu$g); lane 7: nanospheres+DNase+digestion; lane 8: nanopsheres+0.5 $\mu$g DNase; lane 9: nanospheres+0.5 $\mu$g DNase+digestion.

The solid nanospheres protect the DNA from enzymatic degradation (FIG. 16). Stability studies of the DNA-chitosan nanospheres were conducted in 10% fetal bovine serum (FBS), where the nuclease decomposed the DNA. Gel electrophoretic mobility analysis indicated naked DNA incubated for 15 minutes in the serum showed clear indication (Lane 5), whereas the DNA in the nanosphere remained intact (Lanes 6 and 7). Even at a 5-fold higher nuclease concentration of 0.5 ug/ml, there was still no sign of degradation (Lanes 8 and 9).

Figure 17:
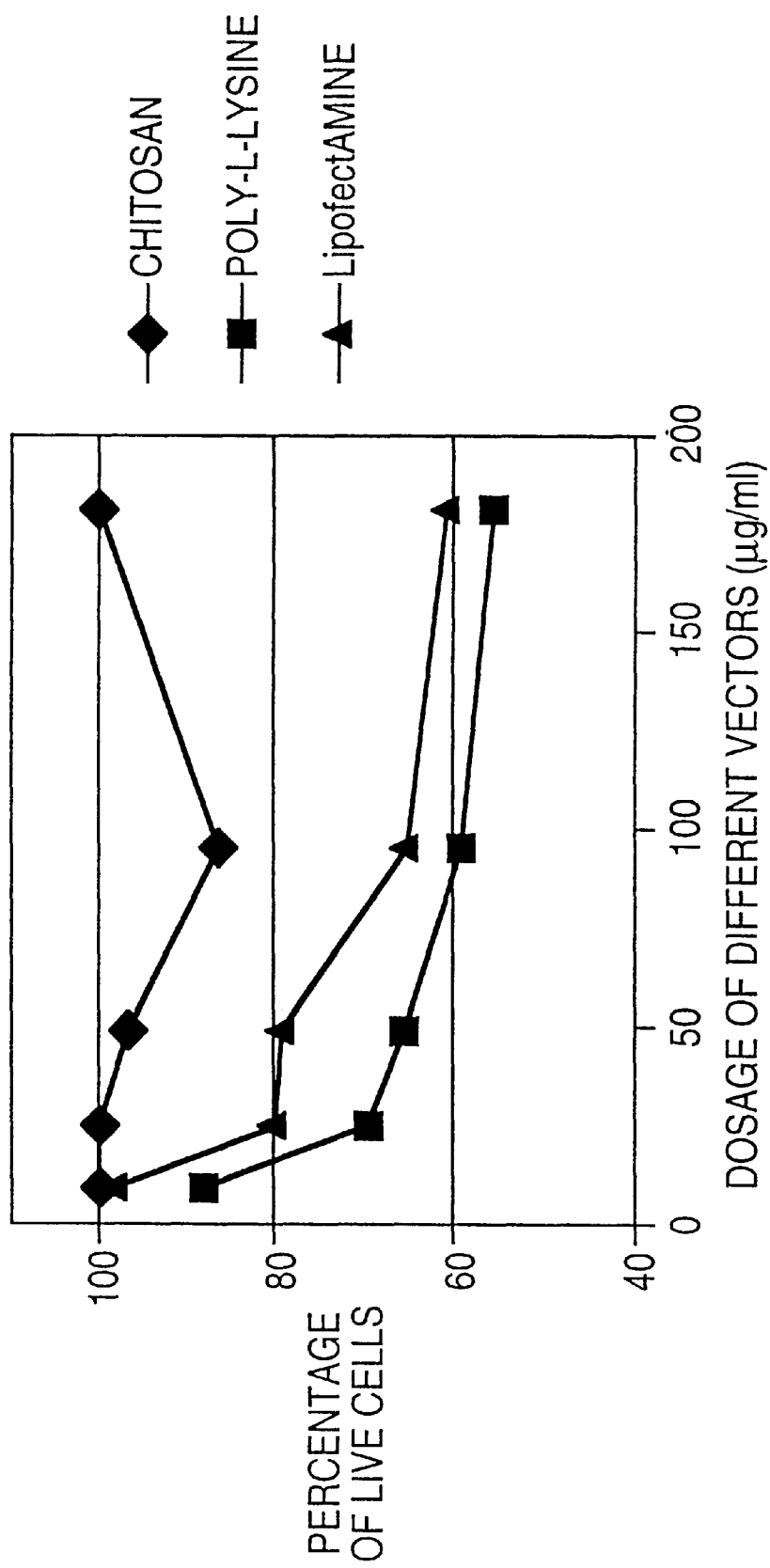
FIG. 17. Cytotoxicity of polycationic gene carriers. HEK 293 cells (4 $\times 10^4$/ well) wee plated in 96-well plates. Different concentrations of chitosan, poly-L-lysine and Lipofectamine were added 24 hrs. later. After 48 hrs cytotoxicity was determined by an MTT (3-[4,5-dimethylthiazol-2-yl]-2,5-diphenyltetrazolium bromide; thiaolylblue)reaction assay according to a standard protocol. Diamonds: chitosan; squares: poly-L-lysine; triangles: lipofectamine.
Figure 18:
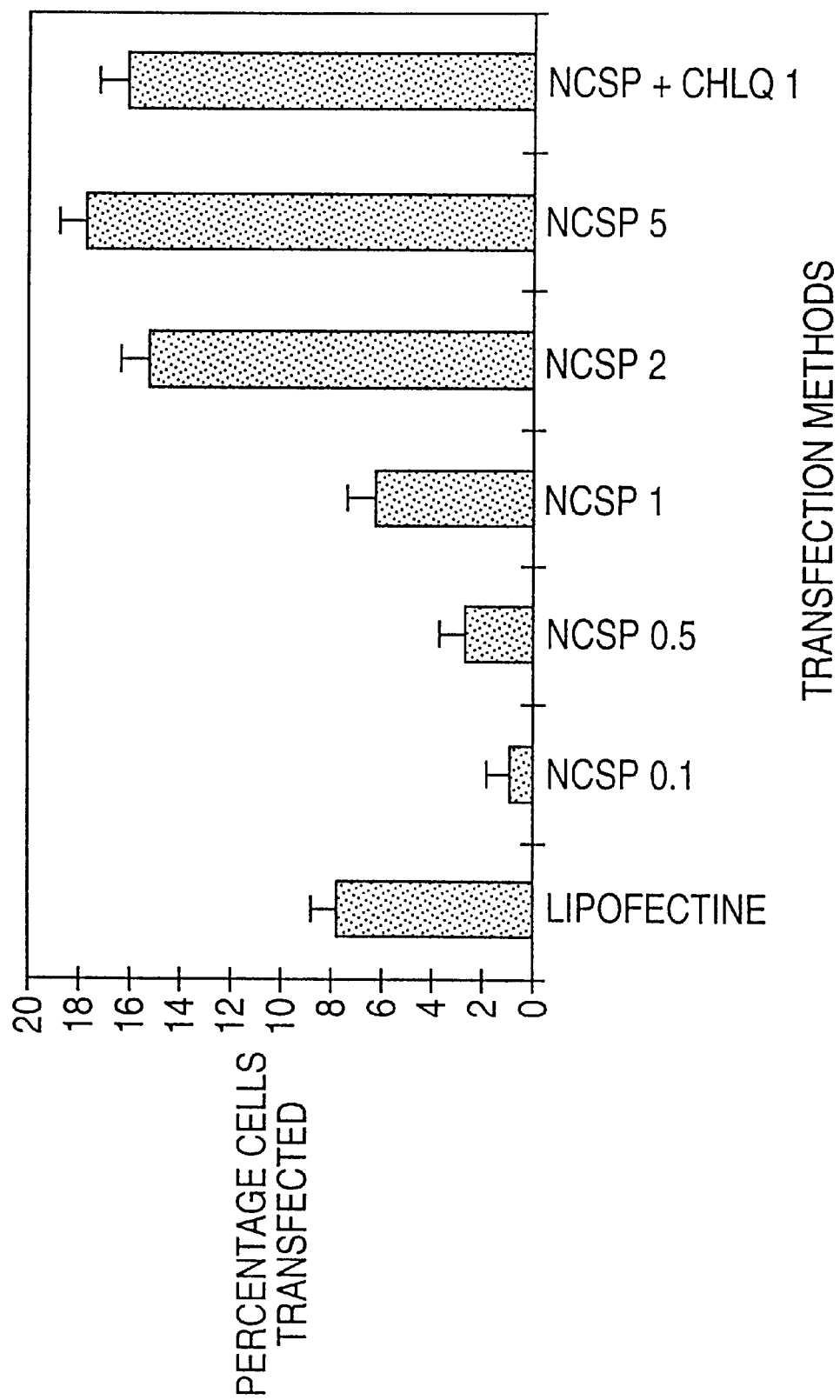
FIG. 18. Green fluorescence protein expression in HEK 293 cells 2 days after transfection. Transfections were carried out in a 24 well plate ($5 \times 10^4$ cells/well) using different amounts of nanospheres. Transfected cells were sorted after 2 days using FACscan. Ncsp 0.1=nanospheres with 0.1 $\mu$g DNA, Ncsp 0.5=nanospheres with 0.5 $\mu$g of DNA, etc. Scsp+Chlq 1=nanospheres with chloroquine and 1 $\mu$g of DNA.
Figure 19:
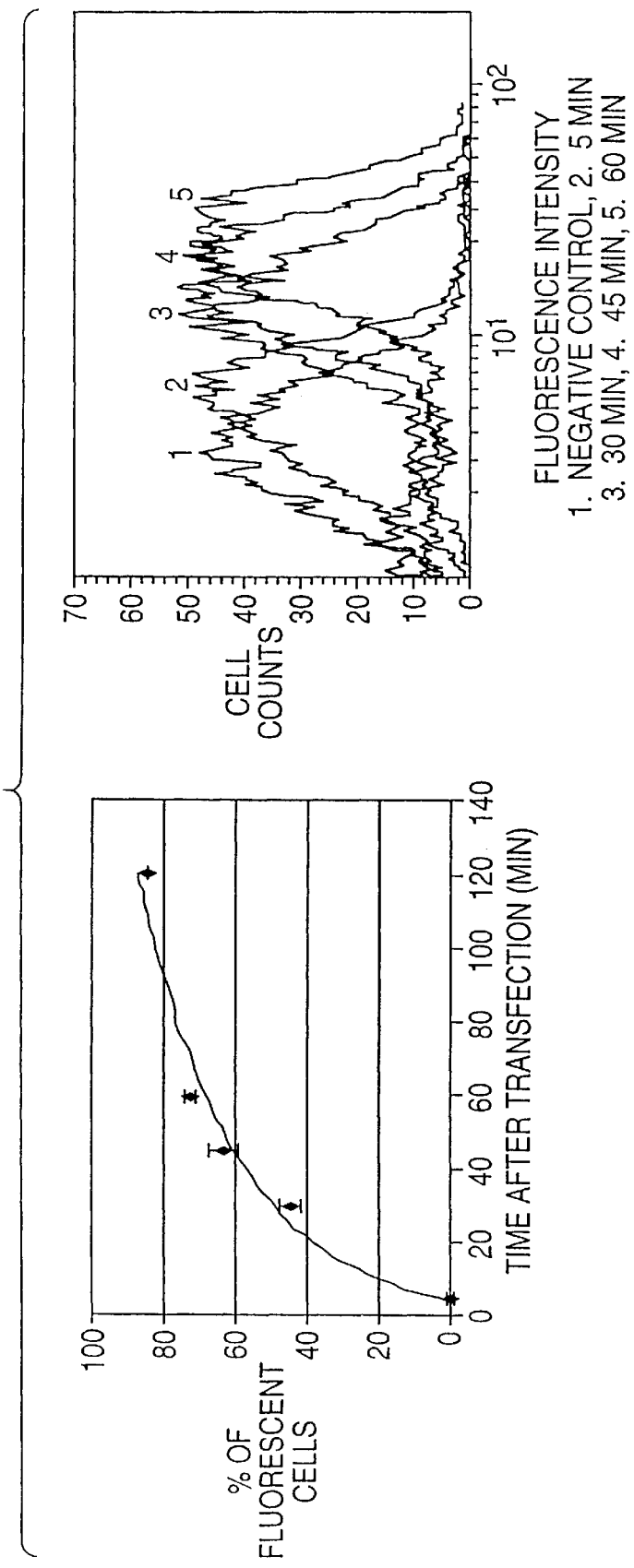
FIG. 19. Uptake of nanospheres in HEK 293 cells. Nanospheres were made with the luciferase plasmid and stained with TO-PRO (Molecular Probes Inc.), a cell-impermeable DNA-binding dye. Cells were washed, trypsinized at different time points arter transfection and analyzed by FACscan. Cells transfected at 4° C. were used as controls to account for particles bound to cell surface.

The cytotoxicity of chitosan was compared to other polycationic gene carriers (FIG. 17). Chitosan was nontoxic at least up to a concentration of 200 ug/ml. The DNA-chitosan nanospheres containing the GFP DNA transfected the 293 cells in a dose-responsive manner (FIG. 18). Uptake of the DNA-chitosan nanospheres was rapid as demonstrated by FACScan analysis (FIG. 19). Almost 100% of cells have taken up the nanospheres in 2 hours of incubation, displaying saturable kinetics.

Figure 20:
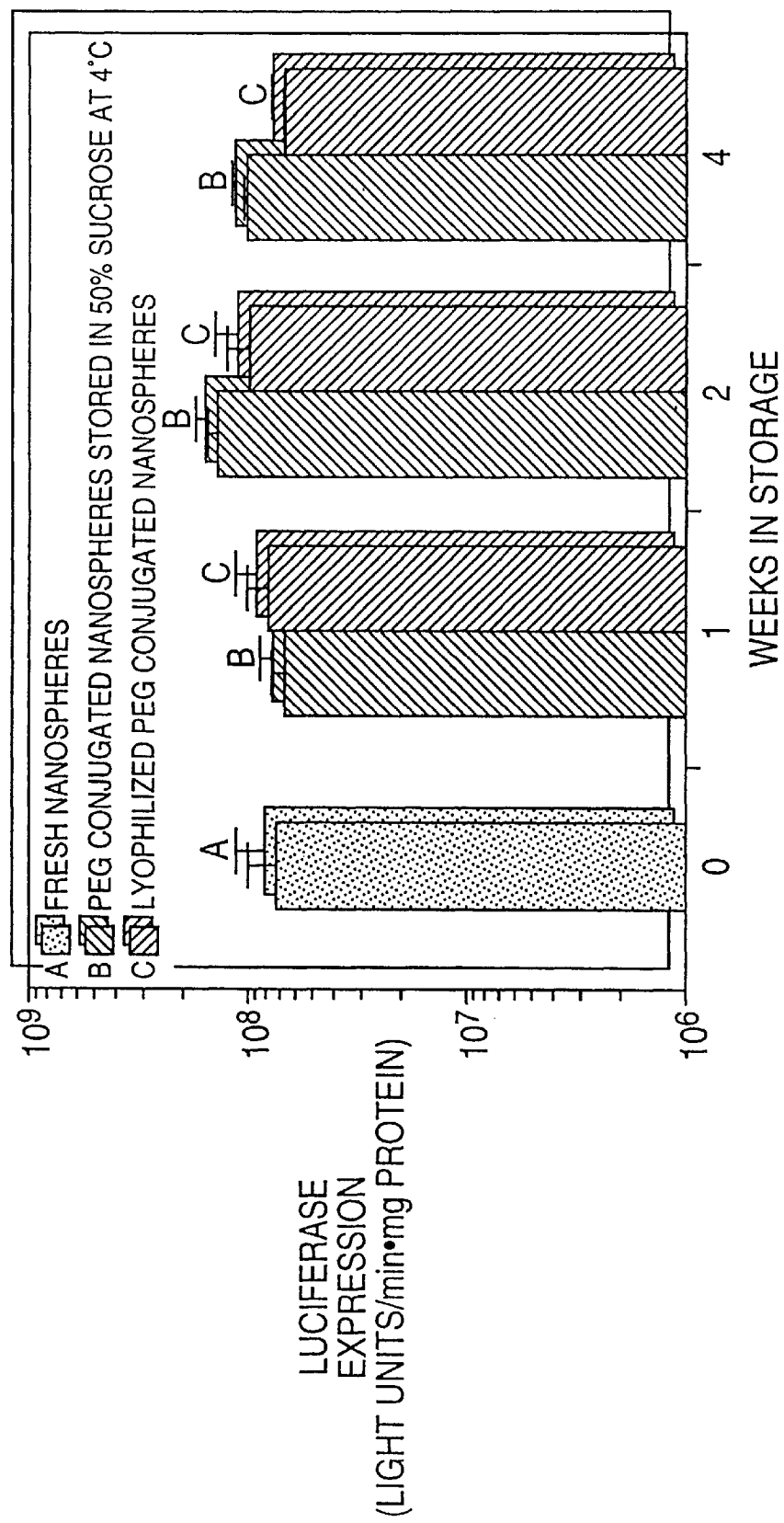
FIG. 20. Storage stability of DNA-chitosan nanospheres and freeze-dried nanospheres. Nanospheres were made according to methods described below. PEG-conjugated nanosphers were freeze dried directly after being spun down to sucrose gradients (50%). Transfection of HEK 293 cells was performed according to the same method as before.
Figure 21:
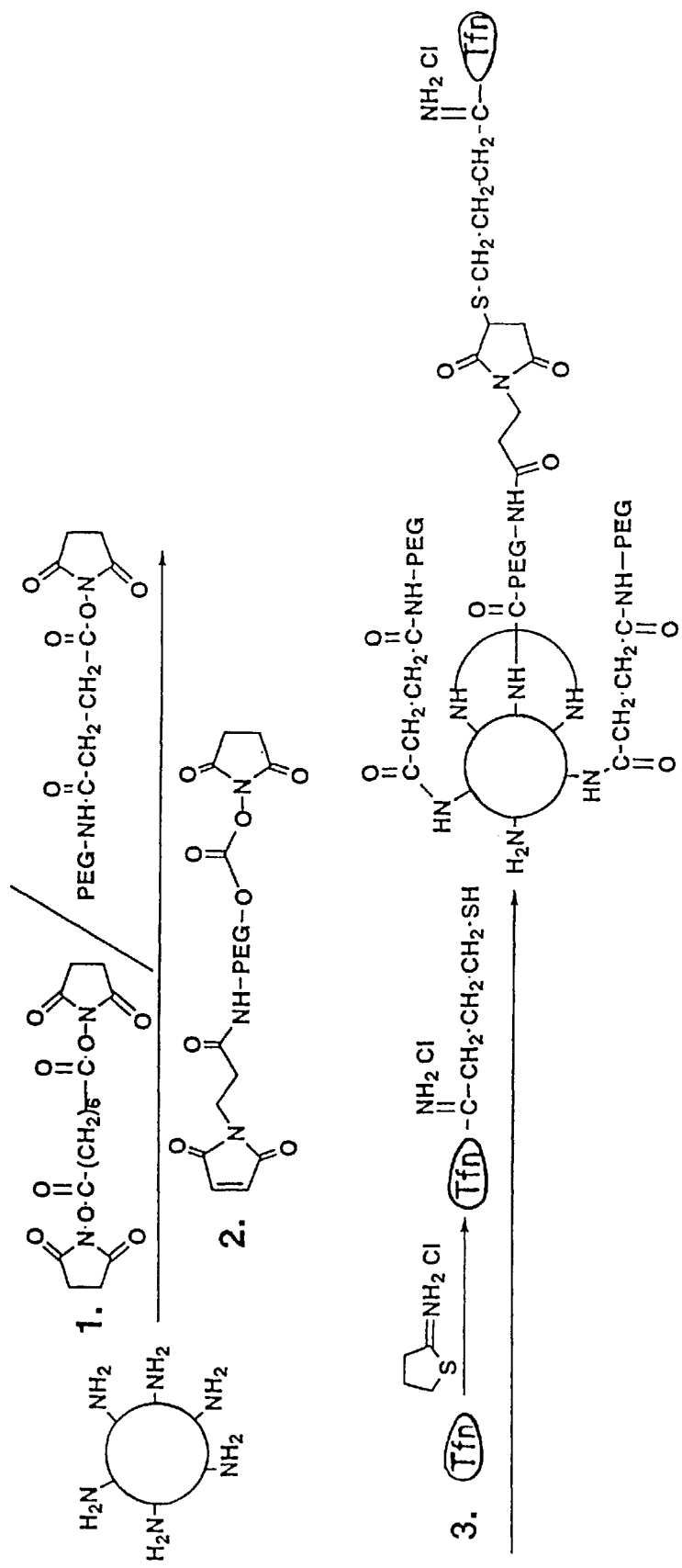
FIG. 21. Chemical scheme for attaching ligands to the surface of the DNA nanospheres.

To allow lyophilization without aggregation, nanospheres were derivatized according to the chemical scheme shown in FIG. 21. One mL of DNA-chitosan nanospheres suspension containing 50 mg of pcDNA was mixed with 5 mL of DSS solution (10 mM), 10 mL of a-malemidyl-w-N-hydroxysuccinimidyl poly(ethylene glycol) solution (NHS-PEG-MAL, MW 2000, 5 mM), 20 mL of succinimidyl succinamide of methoxy poly(ethylene glycol) solution (SSA-PEG, MW 5000, 10 mM) and 100 mL of PBS buffer under vortexing. The mixture was stirred at room temperature for 30 min before 50 mL of 1 M glycine was added to quench the reaction, followed by adding 250 mg of trans-ferrin modified with sulfhydryl group (free sulfhydryl groups were introduced into transferrin by 2-iminothiolane reaction, modification degree was 3~6 per transferring. After reaction for 2 hours at room temperature, the mixture was ultracentrifuged at 50,000 g for 20 min in a 55% sucrose gradient. The nanospheres isolated were lyophilized directly. Conjugation of PEG5000 to the surface of the nanospheres minimized any aggregation in solution. These nanospheres could also be lyophilized without any anti-caking agent and easily resuspended. Transfection efficiency of the nanospheres was not affected by this PEG derivatization (FIG. 20). Neither was it affected by storage in sucrose solution or in the lyophilized state.

Figure 22:
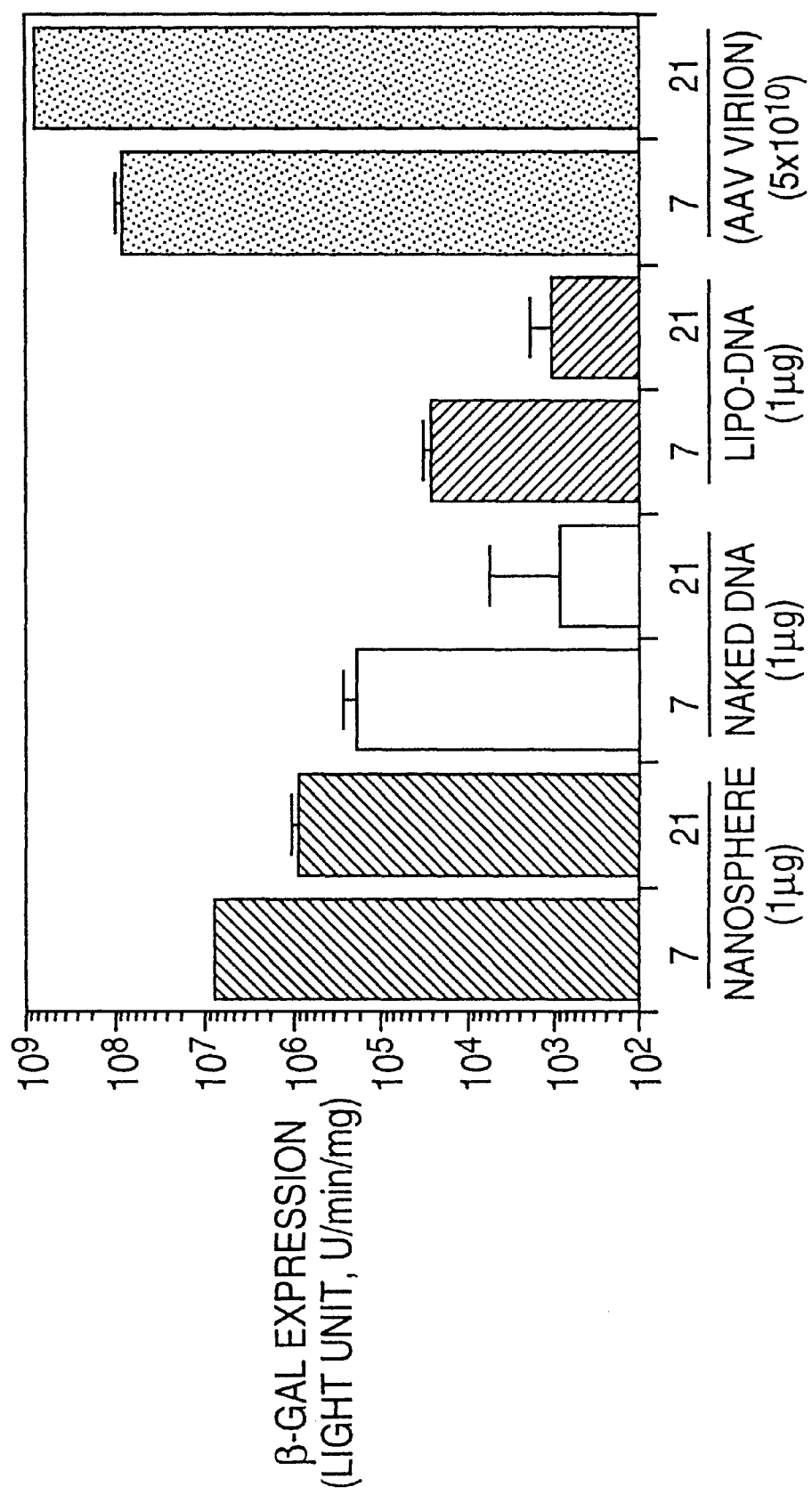
FIG. 22. Expression of β-gal in muscle of BALB/c mice transfected with pcBLacZ gene delivered in different forms. Levels were determined at days 7 and 21 post-transfection, and the endogenous background galactosidase activity was subtracted. Values are average (n=6)+SD.

Comparison of in vivo transfection efficiency was conducted by injecting gelatin nanospheres containing the LacZ plasmid (1 mg total DNA), DNA-Lipofectamine complex (1 mg total DNA), naked plasmid DNA (1 mg), or 5×1010 viral particles of AAV-LacZ suspended in 20 ml into the exposed tibialis anterior muscle bundles of six-week old BALB/c mice. One and three weeks later, the muscle was isolated, homogenized, and the reporter gene expression determined by an assay kit (Galacto-Light') supplied by Tropix (Bedford, Mass.). Injection of gelatin nanospheres containing 1 mg of the LacZ gene into the tibialis muscle bundle of mice produced β-gal expression for at least 21 days (FIG. 22). The level for an equivalent dose of naked DNA was 10–30 fold lower at day 7, and declined to background level by day 21. In contrast to their relative performance in vitro, the Lipofectamine complexes were not as efficient as the nanospheres. The expression level at day 7 was even lower than that of naked DNA. By gross observation, there was acute inflammatory response in the muscle tissue treated by the Lipofectamine complexes, which might account for the poor result. The AAV vector was the most efficient, eliciting a β-gal expression of 50–100 times higher than that of the nanospheres at day 7, and the level increased 6–12 fold further at day 21, probably due to viral replication.

Nanospheres synthesized by salt-induced complex coacervation of cDNA and polycations such as gelatin and chitosan are efficient gene delivery vehicles. DNA-nanospheres in the size range of 200–750 nm could transfect a variety of cell lines. Although the transfection efficiency of the nanospheres was typically lower than that of Lipofectamine and calcium phosphate controls in cell culture, the β-gal expression in muscle of BALB/c mice was higher and more sustained than that achieve by naked DNA and Lipofectamine complexes. This gene delivery system has several attractive features: 1) ligands can be conjugated to the nanosphere to stimulate receptor-mediated endocytosis; 2) lysosomolytic agents can be incorporated to reduce degradation of the DNA in the endosomal and lysosomal compartments; 3) other bioactive agents or multiple plasmids can be co-encapsulated; 4) bioavailability of the DNA can be improved because of protection from serum nuclease degradation by the matrix; 5) the nanosphere is stable in plasma electrolytes, and can be lyophilized for storage without loss of bioactivity.

We claim:

1. A composition comprising solid nanospheres of less than 3 μm for gene delivery to cells, comprising a polymeric cation and a polyanion, wherein the polyanion consists of nucleic acids, wherein the polymeric cation is a carbohydrate.

2. The composition of claim 1 wherein the polymeric cation is chitosan.

3. The composition of claim 1 wherein said nanospheres comprises greater than 5% (w/w) nucleic acids.

4. The composition of claim 1 wherein said nanospheres comprises greater than 20% (w/w) nucleic acids.

5. The composition of claim 1 wherein said nucleic acids comprise a gene of 2–20 kb.

6. The composition of claim 1 wherein the nanospheres are between about 200 and 300 nm.

7. The composition of claim 1 wherein the nanospheres are less than 2 μm.

8. The composition of claim 1 wherein the nanospheres are less than 1 μm.

9. The composition of claim 1 wherein the nanospheres are less than 151 nm.

10. A method of forming solid nanospheres for gene delivery to specific target cells, comprising the step of:
forming nanospheres of less than 3 μm by coacervation of nucleic acids and a polymeric cation which is a carbohydrate.

11. The method of claim 10 wherein the coacervation is performed in the presence of sodium sulfate.

12. The method of claim 10 wherein the polymeric cation is chitosan.

13. The method of claim 10 wherein the polymeric cation is present at a concentration of about 0.01–7% in the step of coacervation.

14. The method of claim 10 wherein the nucleic acids are present in a concentration of 1 ng/ml to 500 μg/ml in the step of coacervation.

15. The method of claim 11 wherein the concentration of sodium sulfate is between about 5 and 100 mM in the step of coacervation.

16. The method of claim 10 wherein the nanospheres are between about 200 and 300 nm.

17. The method of claim 10 wherein the nanospheres are less than 2 μm.

18. The method of claim 10 wherein the nanospheres are less than 1 μm.

19. The method of claim 10 wherein the nanospheres are less than 151 nm.

20. A method for introducing genes into cells, comprising the steps of:
incubating (a) cells to be transfected, in vitro with (b) solid nanospheres of less than 3 μm comprising polymeric cationic molecules and nucleic acid molecules, whereby the cells are transfected with the nucleic acid molecules, wherein the polymeric cationic molecules are carbohydrates.

21. The method of claim 20 wherein the polymeric cationic molecules are chitosan.

22. The method of claim 20 wherein the nucleic acid is DNA.

23. The method of claim 20 wherein the nucleic acid is RNA.

24. The method of claim 20 wherein the nanospheres are between about 200 and 300 nm.

25. The method of claim 20 wherein the nanospheres are less than 2 μm.

26. The method of claim 20 wherein the nanospheres are less than 1μm.

27. The method of claim 20 wherein the nanospheres are less than 151 nm.

* * * * *